US012624344B2

(12) United States Patent
So et al.

(10) Patent No.: US 12,624,344 B2
(45) Date of Patent: May 12, 2026

(54) VARIANT POLYPEPTIDES HAVING ENHANCED ACTIVITY OF 3-METHYL-2-OXOBUTANOATE HYDROXYMETHYLTRANSFERASE AND MICROORGANISMS FOR PRODUCING PANTOTHENIC OR PANTOIC ACID

(71) Applicant: CJ CheilJedang Corporation, Seoul (KR)

(72) Inventors: Yee-Seul So, Seoul (KR); Kwang Soo Shin, Seoul (KR); Jihyun Shim, Seoul (KR); Kwang Woo Lee, Seoul (KR); Yeon-Jae Jang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 219 days.

(21) Appl. No.: 17/776,363

(22) PCT Filed: Mar. 18, 2022

(86) PCT No.: PCT/KR2022/003845

§ 371 (c)(1),
(2) Date: May 12, 2022

(87) PCT Pub. No.: WO2022/239953

PCT Pub. Date: Nov. 17, 2022

(65) Prior Publication Data

US 2025/0290050 A1 Sep. 18, 2025

(30) Foreign Application Priority Data

May 10, 2021 (KR) ........................ 10-2021-0060009

(51) Int. Cl.

*C12N 9/10* (2006.01)
*C12N 15/77* (2006.01)
*C12P 7/42* (2006.01)
*C12P 13/02* (2006.01)
*C12R 1/15* (2006.01)

(52) U.S. Cl.

CPC ........... *C12N 9/1014* (2013.01); *C12N 15/77* (2013.01); *C12P 7/42* (2013.01); *C12P 13/02* (2013.01); *C12R 2001/15* (2021.05); *C12Y 201/02011* (2013.01)

(58) Field of Classification Search

CPC ......... C12N 9/1014; C12N 15/77; C12P 7/42; C12P 13/02; C12R 2001/15; C12Y 201/02011; C07K 14/245

See application file for complete search history.

(56) References Cited

U.S. PATENT DOCUMENTS 6,177,264 B1 1/2001 Eggeling et al.
7,718,205 B2 5/2010 Eisele
2003/0124682 A1 7/2003 Hermann
2005/0089971 A1 4/2005 Rieping
2012/0070870 A1 3/2012 Way et al.

FOREIGN PATENT DOCUMENTS

EP 2157174 2/2010
JP 2000-166580 6/2000
JP 2000-228990 8/2000
KR 1992-0007401 8/1992
KR 10-2000-0047829 7/2000
KR 10-2005-0021433 3/2005
KR 100924065 10/2009

OTHER PUBLICATIONS

Miroshnikov et al., UniProtKB accession No. A0A433NE49_9GAMM published May 8, 2019.*

Witkowski et al., Biochemistry 38:11643-11650, 1999.*

Tang et al., Phil Trans R Soc B 368:20120318, 1-10, 2013.*

Seffernick et al., J. Bacteriol. 183(8):2405-2410, 2001.*

Singh et al., Current Protein and Peptide Science 19(1):5-15, 2018.*

Sadowski et al., Current Opinion in Structural Biology 19:357-362, 2009.*

"RecName: Full=3-methyl-2-oxobutanoate hydroxymethyltransferase {ECO:0000256|HAMAP-Rule:MF_00156}; EC=2.1.2.11 {ECO:0000256|HAMAP-Rule:MF_00156}; AltName: Full= Ketopantoate hydroxymethyltransferase {ECO:0000256|HAMAP-Rule:MF_00156}; Short=KPHMT {ECO:0000256|HAMAP-Rule:MF_00156};", UniProt, (Aug. 12, 2020), Database accession No. A0A5V3MTG3, URL: EBI.

Jones, C E et al, "Cloning and sequencing of the *Escherichia coli* panB gene, which encodes ketopantoate hydroxymethyltransferase, and overproduction of the enzyme", Journal of Bacteriology, American Society for Microbiology, US, (Apr. 1, 1993), vol. 175, No. 7, ISSN 0021-9193, pp. 2125-2130.

Zhang, Bo et al., "Metabolic engineering of *Escherichia coli* for d-pantothenic acid production", Food Chemistry, NL, (Oct. 1, 2019), vol. 294, doi:10.1016/j.foodchem.2019.05.044, ISSN 0308-8146, pp. 267-275.

EPO, search report of EP 22727739.9 dated Jun. 22, 2023.

EPO, communication of EP 22727739.9 dated July 4, 20233.

KIPO, A PCT Search Report & Written Opinion of the corresponding PCT application No. PCT/KR2022/003845 dated Jun. 28, 2022.

Zhang, Bo et al. "Metabolic engineering of *Escherichia coli* for d-pantothenic acid production." Food chemistry vol. 294, pp. 267-275, Oct. 2019.

(Continued)

*Primary Examiner* — Delia M Ramirez

(74) *Attorney, Agent, or Firm* — LEX IP MEISTER, PLLC

(57) ABSTRACT

A 3-methyl-2-oxobutanoate hydroxymethyltransferase variant, a microorganism having enhanced activity of 3-methyl-2-oxobutanoate hydroxymethyltransferase, a composition for producing pantothenic acid and/or pantoic acid comprising the microorganism, and a method for preparing pantothenic acid and/or pantoic acid comprising culturing the microorganism are provided.

6 Claims, No Drawings

Specification includes a Sequence Listing.

(56) References Cited

OTHER PUBLICATIONS

Jones, C. E., et al. "Cloning and sequencing of the *Escherichia coli* panB gene, which encodes ketopantoate hydroxymethyltransferase, and overexpression of the enzyme." Journal of bacteriology 175.7 (Apr. 1993): 2125-2130.
JPO, Office Action of JP 2023-568679 dated Oct. 30, 2024, total 11 pages.
3, 2-methyl-oxobutanoate hydroxymethyltransferase [*Salmonella enterica*], Database GenBank [online], EBT9665916,2019 , Internet <URL: https://www.ncbi.nlm.nih.gov/protein/EBT9665916.1>, [Search on Oct. 23, Reiwa 6(2024)], [2, Jan. 2006], total 2 pages.
GenBank Accession No. AFG39014.1"3-methyl-2-oxobutanoate hydroxymethyltransferase [*Escherichia coli* P12b]" (Jan. 31, 2014).
KIPO, Office Action of the corresponding Korean Patent Application No. 10-2021-0060009 dated Feb. 22, 2023.
Samuel Karlin et al., "Applications and statistics for multiple high-scoring segments in molecular sequences", Pro. Natl. Acad. Sci. USA, vol. 90, pp. 5873-5877, Jun. 1993.
William R. Pearson, "[S] Rapid and Sensitive Sequence Comparison with FASTP and FASTA", Methods Enzymol., 183, 63, 1990.
Sambrook et al., supra,9.50-9.51, 11.7-11.8, Molecular Cloning, A Laboratory Manual, vol. 2, Third Edition.
Satoshi Takeda et al., "Detection of K-ras Mutation in Sputum by Mutant-Allele-Specific Amplification (MASA)", Hum. Mutation, 2, 112-117 (1993).

* cited by examiner

VARIANT POLYPEPTIDES HAVING ENHANCED ACTIVITY OF 3-METHYL-2-OXOBUTANOATE HYDROXYMETHYLTRANSFERASE AND MICROORGANISMS FOR PRODUCING PANTOTHENIC OR PANTOIC ACID

TECHNICAL FIELD

Cross-Reference to Related Application(S)

The present application claims the priority based on Korean Patent Application No. 10-2021-0060009 filed on May 10, 2021, and all the contents disclosed in the document of the corresponding Korean Patent Application are incorporated by reference as a part of the present description.

A 3-methyl-2-oxobutanoate hydroxymethyltransferase variant, a microorganism having enhanced activity of 3-methyl-2-oxobutanoate hydroxymethyltransferase, a composition for producing pantothenic acid and/or pantoic acid comprising the microorganism, and a method for preparing pantothenic acid and/or pantoic acid comprising culturing the microorganism are provided.

BACKGROUND ART

Pantothenic acid is a substance belonging to the vitamin B complex, also called vitamin B5, and is one of commercially important substances that are variously applied to cosmetics, medicines, human nutrition, animal nutrition, and the like. Pantothenic acid is a structure in which beta-alanine is linked to pantoic acid by an amide bond.

Pantothenic acid or pantoic acid may be prepared by chemical synthesis, or may be prepared biotechnologically by fermenting an appropriate microorganism in a suitable medium. An advantage of the biotechnological preparation method using a microorganism is that a desired stereoisomeric D-form of pantothenic acid or pantoic acid is formed.

Accordingly, it is required to develop a microorganism having an advantageous effect in biotechnologically preparing pantothenic acid and/or pantoic acid and a technology for preparing pantothenic acid and/or pantoic acid with high efficiency using the same.

PRIOR ART

Patent Document (Prior document 1) U.S. Registered U.S. Pat. No. 7,718,205

DISCLOSURE

Technical Problem

One example of the present application provides a polypeptide having 3-methyl-2-oxobutanoate hydroxymethyltransferase activity. In one embodiment, (1) the polypeptide may comprise the amino acid sequence in which an amino acid corresponding to the 159th residue from the N-terminus in the amino acid sequence of SEQ ID NO: 37 is substituted with another amino acid. In another embodiment, (2) the polypeptide may comprise the amino acid sequence in which an amino acid corresponding to the 159th residue from the N-terminus is substituted with another amino acid and the 116th residue from the N-terminus is substituted with another amino acid in the amino acid sequence of SEQ ID NO: 37. Counting amino acids from the N-terminus in the amino acid sequence as described above may mean counting with methionine (Met, M) translated from the initiation codon as the first amino acid.

Another example, provides a polynucleotide encoding the polypeptide.

Other example, provides a recombinant vector comprising the polynucleotide. The recombinant vector, may be an expression vector.

Other example provides a microorganism producing pantothenic acid or pantoic acid, which comprises one or more (one, two or all) selected from the group consisting of the polypeptide, polynucleotide encoding the polypeptide, and recombinant vector comprising the polynucleotide, and has enhanced activity of 3-methyl-2-oxobutanoate hydroxymethyltransferase.

The microorganism, may comprise (1) one or more (one, two or all) selected from the group consisting of a polypeptide in which an amino acid corresponding to the 159th residue from the N-terminus in the amino acid sequence of SEQ ID NO: 37 is substituted with another amino acid, a polynucleotide encoding the polypeptide and a recombinant vector comprising the polynucleotide; or (2) (1) above, and one or more (one, two or all) selected from the group consisting of a polypeptide in which an amino acid corresponding to the 116th residue from the N-terminus in the amino acid sequence of SEQ ID NO: 37 is substituted with another amino acid, a polynucleotide encoding the polypeptide and a recombinant vector comprising the polynucleotide.

The microorganism may be a genus *Corynebacterium* microorganism or a genus *Escherichia* microorganism. The genus *Corynebacterium* microorganism may be *Corynebacterium glutamicum.*

Other example, provides a composition for producing pantothenic acid or pantoic acid, comprising the microorganism.

Other example, provides a use of the microorganism in production of pantothenic acid and/or pantoic acid.

Other example, provides a method for preparation of pantothenic acid or pantoic acid, comprising culturing the microorganism in a medium. The method for preparation may further comprise recovering pantothenic acid or pantoic acid from the cultured microorganism, medium or both of them, after the culturing.

Technical Solution

The present description is to provide a recombinant strain with excellent production ability of pantothenic acid and/or pantoic acid, by searching 3-methyl-2-oxobutanoate hydroxymethyltransferase or its variant which can enhance the production ability of pantothenic acid and/or pantoic acid and introducing this to a microorganism.

In the present description, it was confirmed that the microorganism expressing 3-methyl-2-oxobutanoate hydroxymethyltransferase had excellent production ability of pantothenic acid, and it was confirmed that the production ability of pantothenic acid was further increased, when an amino acid substitution mutation was introduced to a specific position of 3-methyl-2-oxobutanoate hydroxymethyltransferase.

One example provides a polypeptide having 3-methyl-2-oxobutanoate hydroxymethyltransferase activity. In one embodiment, the polypeptide may comprise the amino acid sequence in which an amino acid corresponding to the 159th residue from the N-terminus in the amino acid sequence of SEQ ID NO: 37 is substituted with another amino acid. In another embodiment, the polypeptide may comprise the amino acid sequence in which an amino acid corresponding to the 159th residue from the N-terminus is substituted with another amino acid and an amino acid corresponding to the 116th residue from the N-terminus is substituted with another amino acid in the amino acid sequence of SEQ ID NO: 37. Counting amino acids from the N-terminus in the amino acid sequence as described above may mean counting with methionine (Met, M) translated from the initiation codon as the first amino acid.

Another example, provides a polynucleotide encoding the polypeptide.

Other example, provides a recombinant vector comprising the polynucleotide. The recombinant vector, may be used as an expression vector of the polypeptide.

Other example provides a microorganism with enhanced activity of 3-methyl-2-oxobutanoate hydroxymethyltransferase. The microorganism may be a microorganism producing pantothenic acid or pantoic acid.

That the activity of 3-methyl-2-oxobutanoate hydroxymethyltransferase is enhanced, may be enhanced by that microbial endogenous 3-methyl-2-oxobutanoate hydroxymethyltransferase is mutated or exogenous 3-methyl-2-oxobutanoate hydroxymethyltransferase or variant thereof is introduced.

In one embodiment, the 3-methyl-2-oxobutanoate hydroxymethyltransferase with enhanced activity may comprise the amino acid sequence in which an amino acid corresponding to the 159th residue from the N-terminus in the amino acid sequence of SEQ ID NO: 37 is substituted with another amino acid. Otherwise, the 3-methyl-2-oxobutanoate hydroxymethyltransferase with enhanced activity may comprise the amino acid sequence in which an amino acid corresponding to the 159th residue from the N-terminus is substituted with another amino acid, and an amino acid corresponding to the 116th residue from the N-terminus is substituted with another amino acid in the amino acid sequence of SEQ ID NO: 37.

The microorganism with enhanced activity of 3-methyl-2-oxobutanoate hydroxymethyltransferase, may comprise, (1) one or more selected from the group consisting of a polypeptide in which an amino acid corresponding to the 159th residue from the N-terminus in the amino acid sequence of SEQ ID NO: 37 is substituted with another amino acid, a polynucleotide encoding the polypeptide and a recombinant vector comprising the polynucleotide; or (2) (1) above, and one or more selected from the group consisting of a polypeptide in which an amino acid corresponding to the 116th residue from the N-terminus in the amino acid sequence of SEQ ID NO: 37 is substituted with another amino acid, a polynucleotide encoding the polypeptide and a recombinant vector comprising the polynucleotide.

The microorganism with enhanced activity of 3-methyl-2-oxobutanoate hydroxymethyltransferase, may have higher production ability of pantothenic acid and/or pantoic acid, compared to a homogeneous microorganism in which 3-methyl-2-oxobutanoate hydroxymethyltransferase is not enhanced (for example, an amino acid corresponding to the 159th residue and/or an amino acid corresponding to the 116th residue from the N-terminus in the amino acid sequence of SEQ ID NO: 37 is not substituted with another amino acid).

Other example provides a composition for producing pantothenic acid and/or pantoic acid comprising the microorganism with enhanced activity of 3-methyl-2-oxobutanoate hydroxymethyltransferase.

Other example provides a method for producing pantothenic acid and/or pantoic acid comprising culturing the microorganism with enhanced activity of 3-methyl-2-oxobutanoate hydroxymethyltransferase.

Hereinafter, it will be described in more detail.

Polypeptide

In the present description, pantothenic acid (e.g., D-pantothenic acid) is a compound having the structure of Chemical formula 1, and is a vitamin (vitamin B5) in which β-alanine is linked to pantoic acid by an amide bond, and is a component of coenzyme A (CoA) and acyl carrier protein (ACP), and is involved in various metabolic processes of living organisms.

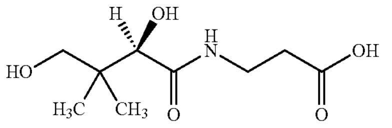

(Chemical formula 1: pantothenic acid)

Pantoic acid (e.g., D-pantoic acid) is a compound having the structure of Chemical formula 2, and is a component of various biological activity compounds:

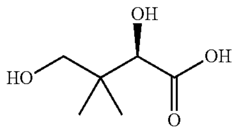

(Chemical formula 2: pantothenic acid)

In the present description, 3-methyl-2-oxobutanoate hydroxymethyltransferase is an enzyme catalyzing a process of biosynthesizing tetrahydrofolate and 2-dihydropantoate from 5,10-methylenetetrahydrofolate, 3-methyl-2-oxobutanoate, and water.

In one embodiment, the 3-methyl-2-oxobutanoate hydroxymethyltransferase may be variant in which a mutation in which one or more amino acid residues are substituted, deleted or inserted is introduced.

In one example, the variant of 3-methyl-2-oxobutanoate hydroxymethyltransferase may be one in which an amino acid corresponding to the 159th residue of the amino acid sequence of SEQ ID NO: 37 is substituted with an amino acid, that is an amino acid which is selected from the group consisting of arginine (R), histidine (H), lysine (K), aspartic acid (D), glutamic acid (E), serine(S), threonine (T), asparagine (N), glutamine (Q), cysteine (C), proline (P), valine (V), isoleucine (I), leucine (L), methionine (M), tyrosine (Y), phenylalanine (F), tryptophane (W), and glycine (G) and is different from the original amino acid. In one embodiment, the 3-methyl-2-oxobutanoate hydroxymethyltransferase variant may be one in which an amino acid corresponding to the 159th residue in the amino acid sequence of SEQ ID NO: 37 is substituted with another amino acid, that is, arginine (R), histidine (H), lysine (K), aspartic acid (D), glutamic acid (E), serine(S), threonine (T), asparagine (N), glutamine (Q), cysteine (C), proline (P), valine (V), isoleucine (I), leucine (L), methionine (M) or tyrosine (Y). It is obvious that among the variants, even if some amino acid sequences except for the amino acid corresponding to the 159th residue in the amino acid sequence of SEQ ID NO: 37 are deleted, modified, substituted or added, as long as they show the activity of 3-methyl-2-oxobutanoate hydroxymethyltransferase, they may be included in the variant of the present application.

In addition, in one example, the variant may comprise a polypeptide in which an amino acid corresponding to the 159th residue of the amino acid sequence of SEQ ID NO: 37 in the amino acid sequence having homology or identity of at least 80%, 85%, 90%, 91%, 92%, 93%, 94%, 95%, 96%, 97%, 98%, or 99% or more, to the amino acid sequence disclosed as SEQ ID NO: 37 is substituted with another amino acid. In other words, a polypeptide which comprises a substitution at the position corresponding to the 159th residue of the amino acid sequence of SEQ ID NO: 37, has sequence homology or identity of at least 80%, 90%, 95%, 96%, 97%, 98%, or 99% or more and less than 100%, to the amino acid sequence of SEQ ID NO: 37, and has 3-methyl-2-oxobutanoate hydroxymethyltransferase activity may be included in the variant of the present application.

In one embodiment, the 3-methyl-2-oxobutanoate hydroxymethyltransferase variant may comprise an amino acid sequence selected from SEQ ID NO: 110 to SEQ ID NO: 125, but not limited thereto. It is obvious that even if some amino acid sequences except for the amino acid corresponding to the 159th residue are deleted, modified, substituted or added in the variant consisting of any one sequence selected from SEQ ID NO: 110 to SEQ ID NO: 125, as long as they show the activity of 3-methyl-2-oxobutanoate hydroxymethyltransferase, they may be included in the variant of the present application. In addition, in one example, the variant may comprise a polypeptide having homology or identity of at least 80%, 85%, 90%, 91%, 92%, 93%, 94%, 95%, 96%, 97%, 98%, or 99% or more to any one amino acid sequence selected from SEQ ID NO: 110 to SEQ ID NO: 125 in which an amino acid corresponding to the 159th residue of the amino acid sequence of SEQ ID NO: 37 is fixed. In other words, a polypeptide which comprises a substitution with another amino acid at a position corresponding to the 159th residue of the amino acid sequence of SEQ ID NO: 37 and has sequence homology or identity of at least 80%, 90%, 95%, 96%, 97%, 98%, or 99% or more and less than 100% to any one amino acid sequence selected from SEQ ID NO: 110 to SEQ ID NO: 125 and has 3-methyl-2-oxobutanoate hydroxymethyltransferase activity may be included in the variant of the present application.

In one example, in the variant of 3-methyl-2-oxobutanoate hydroxymethyltransferase, (1) an amino acid of 3-methyl-2-oxobutanoate hydroxymethyltransferase corresponding to the 159th residue in the amino acid sequence of SEQ ID NO: 37 may be substituted with another amino acid which is selected from the group consisting of arginine (R), histidine (H), lysine (K), aspartic acid (D), glutamic acid (E), serine (S), threonine (T), asparagine (N), glutamine (Q), cysteine (C), proline (P), valine (V), isoleucine (I), leucine (L), methionine (M) and tyrosine (Y), and is different from the original amino acid, and (2) an amino acid of 3-methyl-2-oxobutanoate hydroxymethyltransferase corresponding to the 116th residue in the amino acid sequence of SEQ ID NO: 37 may be substituted with another amino acid which is selected from the group consisting of aspartic acid (D), glutamic acid (E), serine(S), threonine (T), asparagine (N), glutamine (Q), cysteine (C), alanine (A), valine (V), isoleucine (I), leucine (L) and methionine (M), and is different from the original amino acid.

It is obvious that even if some amino acid sequences except for the amino acid corresponding to the 159th residue and the amino acid corresponding to the 116th residue are deleted, modified, substituted or added in the amino acid sequence of SEQ ID NO: 37, as long as they show the activity of 3-methyl-2-oxobutanoate hydroxymethyltransferase, they may be included in the variant of the present application.

Furthermore, in one example, the variant may comprise a polypeptide in which (1) an amino acid corresponding to the 159th residue of the amino acid sequence of SEQ ID NO: 37 and (2) an amino acid corresponding to the 116th residue of the amino acid sequence of SEQ ID NO: 37 are substituted with another amino acid, in the amino acid sequence having homology or identity of at least 80%, 85%, 90%, 91%, 92%, 93%, 94%, 95%, 96%, 97%, 98%, or 99% or more, to the amino acid sequence disclosed as SEQ ID NO: 37. In other words, a polypeptide which comprises a substitution with another amino acid at (1) a position corresponding to the 159th residue of the amino acid sequence of SEQ ID NO: 37 and (2) a position corresponding to the 116th residue of the amino acid sequence of SEQ ID NO: 37, has sequence homology or identity of at least 80%, 90%, 95%, 96%, 97%, 98%, or 99% or more and less than 100% to the amino acid sequence of SEQ ID NO: 37 and has 3-methyl-2-oxobutanoate hydroxymethyltransferase activity may be comprised in the variant of the present application.

In one embodiment, the 3-methyl-2-oxobutanoate hydroxymethyltransferase variant may comprise the amino acid sequence of SEQ ID NO: 128, but not limited thereto. It is obvious that even if some amino acid sequences except for (1) the amino acid corresponding to the 159th residue and (2) the amino acid corresponding to the 116th residue are deleted, modified, substituted or added in the variant consisting of the amino acid sequence of SEQ ID NO: 128, as long as they show the activity of 3-methyl-2-oxobutanoate hydroxymethyltransferase, they may be included in the variant of the present application. In addition, in one example, the variant the variant may comprise a polypeptide having homology or identity of at least 80%, 85%, 90%, 91%, 92%, 93%, 94%, 95%, 96%, 97%, 98%, or 99% or more to the amino acid sequence of SEQ ID NO: 128 in which (1) an amino acid corresponding to the 159th residue of the amino acid sequence of SEQ ID NO: 37 and (2) an amino acid corresponding to the 116th residue of the amino acid sequence of SEQ ID NO: 37 are fixed. In other words, a polypeptide which comprises a substitution with another amino acid at (1) a position corresponding to the 159th residue of the amino acid sequence of SEQ ID NO: 37 and (2) a position corresponding to the 116th residue of the amino acid sequence of SEQ ID NO: 37, and has sequence homology or identity of at least 80%, 90%, 95%, 96%, 97%, 98%, or 99% or more and less than 100% to the amino acid sequence of SEQ ID NO: 128 and has 3-methyl-2-oxobutanoate hydroxymethyltransferase activity may be included in the variant of the present application.

Microorganism

The present description provides, a microorganism producing pantothenic acid or pantoic acid, comprising (1) one or more selected from the group consisting of a polypeptide in which an amino acid corresponding to the 159th residue from the N-terminus in the amino acid sequence of SEQ ID NO: 37 is substituted with another amino acid, a polynucleotide encoding the polypeptide and a recombinant vector comprising the polynucleotide; or (2) (1) above, and one or more selected from the group consisting of a polypeptide in which an amino acid corresponding to the 116th residue from the N-terminus in the amino acid sequence of SEQ ID NO: 37 is substituted with another amino acid, a polynucleotide encoding the polypeptide and a recombinant vector comprising the polynucleotide.

In the present description, the term "microorganism with enhanced activity of 3-methyl-2-oxobutanoate hydroxymethyltransferase" may be that a microorganism which does not have pantothenic acid and/or pantoic acid production ability has pantothenic acid and/or pantoic acid production ability, or has higher pantothenic acid and/or pantoic acid production ability than the original pantothenic acid and/or pantoic acid production ability, by being engineered (mutated) to express the aforementioned polypeptide having 3-methyl-2-oxobutanoate hydroxymethyltransferase activity. In the present description, "microorganism" encompasses single-celled bacteria, and may be interchangeably with "cell". In the present description, the microorganism before being mutated to express the polypeptide having 3-methyl-2-oxobutanoate hydroxymethyltransferase activity, in order to distinguish from the mutated microorganism, may be expressed as "parent microorganism (or parent strain) or host cell".

In one example, the microorganism may be one or more kinds selected from the group consisting of the genus *Corynebacterium* microorganism and the genus *Escherichia* microorganism and the like. The genus *Corynebacterium* microorganism may include *Corynebacterium glutamicum, Corynebacterium ammoniagenes, Brevibacterium lactofermentum, Brevibacterium flavum, Corynebacterium thermoaminogenes, Corynebacterium efficiens*, and the like, but not necessarily limited thereto. Much more specifically, the genus *Corynebacterium* microorganism may be *Corynebacterium glutamicum*. The genus *Escherichia* strain may be *Escherichia coli.*

In the present description, in the microorganism with enhanced activity of 3-methyl-2-oxobutanoate hydroxymethyltransferase, a gene encoding 3-methyl-2-oxobutanoate hydroxymethyltransferase may be introduced.

In the present description, "microorganism with enhanced activity of 3-methyl-2-oxobutanoate hydroxymethyltransferase" may be a microorganism expressing a polypeptide having 3-methyl-2-oxobutanoate hydroxymethyltransferase activity, in which a mutation (engineering) is introduced so that a parent strain expresses a polypeptide having 3-methyl-2-oxobutanoate hydroxymethyltransferase activity. The microorganism may comprise one or more selected from the group consisting of a polypeptide having 3-methyl-2-oxobutanoate hydroxymethyltransferase activity, a polynucleotide encoding the polypeptide and a recombinant vector comprising the polynucleotide. In one example, the mutation to express the polypeptide having 3-methyl-2-oxobutanoate hydroxymethyltransferase activity may be performed by introducing the aforementioned polynucleotide encoding the polypeptide having 3-methyl-2-oxobutanoate hydroxymethyltransferase activity or recombinant vector comprising the same into a parent strain. The polynucleotide encoding the polypeptide having 3-methyl-2-oxobutanoate hydroxymethyltransferase activity, which is introduced to the parent strain as described above may replace the endogenous gene encoding 3-methyl-2-oxobutanoate hydroxymethyltransferase in the parent strain or be further comprised in addition.

In one embodiment, the microorganism expressing the polypeptide having 3-methyl-2-oxobutanoate hydroxymethyltransferase activity may be Accession No. KCCM12973P (named *Corynebacterium glutamicum* CV03-5002).

In the present description, that a polynucleotide (may be interchangeably used with "gene") or a polypeptide (may be interchangeably used with "protein") "comprises a specific nucleic acid sequence or amino acid sequence, or consists of a specific nucleic acid sequence or amino acid sequence, or is expressed as a specific nucleic acid sequence or amino acid sequence" may mean that the polynucleotide or polypeptide necessarily comprises the specific nucleic acid sequence or amino acid sequence, and it may be interpreted as comprising a "substantially equivalent sequence" in which a mutation (deletion, substitution, modification and/or addition) is added to the specific nucleic acid sequence or amino acid sequence within a range of maintaining the original function and/or desired function of the polynucleotide or polypeptide.

In one example, the nucleic acid sequence or amino acid sequence provided in the present description may include those modified by common mutagenesis methods, for example, direct evolution and/or site-directed mutagenesis, and the like, within a range of maintaining its original function or desired function. In one example, that a polynucleotide or polypeptide "comprises a specific nucleic acid sequence or amino acid sequence, or consists of a specific nucleic acid sequence or amino acid sequence" may mean necessarily comprising (i) the specific nucleic acid sequence or amino acid sequence, or (ii) consisting of or necessarily comprising an amino acid sequence having homology of 60% or more, 70% or more, 80% or more, 85% or more, 90% or more, 91% or more, 92% or more, 93% or more, 94% or more, 95% or more, 96% or more, 97% or more, 98% or more, 99% or more, 99.5% or more, or 99.9% or more to the specific nucleic acid sequence or amino acid sequence within a range of maintaining the original function and/or desired function. In the present description, the desired function may refer to a function of increasing or giving pantothenic acid and/or pantoic acid production ability of a microorganism.

In the nucleic acid sequence disclosed in the present description, various modifications may be made o the coding region, within a range that does not change the amino acid sequence and/or function of a protein expressed from the coding region, in consideration of a codon preferred in a microorganism to express the protein (lysine excretion protein) due to degeneracy of the codon.

In the present description, the term "homology (identity)" refers to a degree of correspondence with a given nucleic acid sequence or amino acid sequence and may be expressed as a percentage (%). In case of the homology to the nucleic acid sequence, it may be determined using for example, algorithm BLAST by documents (See: Karlin and Altschul, Pro. Natl. Acad. Sci. USA, 90, 5873, 1993) or FASTA by Pearson (See: Methods Enzymol., 183, 63, 1990). Based on this algorithm BLAST, programs called BLASTN or BLASTX have been developed.

In one example, the polynucleotide comprising the specific nucleic acid sequence provide in the present description may be interpreted as including polynucleotide fragments comprising the specific nucleic acid sequence or substantially equivalent nucleic acid sequence thereto, as well as a complementary nucleic acid sequence to the specific nucleic acid sequence. Specifically, the polynucleotide having complementarity may be hybridized at a Tm value which can be appropriately controlled by those skilled in the art, if necessary, for example, a Tm value of 55° C., 60° C., 63° C. or 65° C., and may be analyzed under the condition described below: this condition is specifically disclosed in known documents. For example, a condition in which genes having high complementarity of 60% or more, 70% or more, 80% or more, 85% or more, 90% or more, 91% or more, 92% or more, 93% or more, 94% or more, 95% or more, 96% or more, 97% or more, 98% or more, 98% or more, 99.5% or more, or 99.9% or more are hybridized, and genes having complementarity lower than that are not hybridized, or a common southern hybridization washing condition, which is a condition of washing once, specifically, twice or three times, at a salt concentration and temperature, corresponding to 60° C., 1×SSC (saline-sodium citrate buffer), and 0.1% (w/v) SDS (Sodium Dodecyl Sulfate); 60° C., 0.1×SSC, and 0.1% SDS; or 68° C., 0.1×SSC, and 0.1% SDS, and the like may be listed, but not limited thereto. Hybridization requires that two nucleotides n have complementary sequences, or mismatches between bases may be allowed depending on the stringency of hybridization. The term "complementary" may be used to describe a relationship between nucleotide bases capable of hybridizing to each other. For example, in case of DNA, adenosine is complementary to thymine and cytosine is complementary to guanine. The appropriate stringency for hybridizing polynucleotides depends on the length and degree of complementarity of the polynucleotides, which are well known in the art (See Sambrook et al., supra, 9.50-9.51, 11.7-11.8).

The introduction of the polynucleotide or vector may be performed by selecting a known transformation method by those skilled in the art. In the present description, the term "transformation" is a process of introducing a specific polynucleotide or a vector comprising the same into a host cell, and the transformed polynucleotide may be located as inserted into a chromosome or located extrachromosomally in a host cell. As one example, transformation may make a protein encoded by the polynucleotide expressed in a host cell by introducing a polynucleotide encoding a target protein (foreign protein) or a vector comprising the same. In addition, the polynucleotide may comprise DNA and/or RNA encoding a target protein. As long as the polynucleotide may be introduced and expressed into a host cell, the form to be introduced is not limited. For example, the polynucleotide may be introduced into a host cell in the form of an expression cassette, which is a gene construct comprising all elements necessary for self-expression. The expression cassette may comprise expression control elements such as a promoter, a transcription termination signal, a ribosome binding site and/or a translation termination signal, which are operably linked to the polynucleotide in general. The expression cassette may be in the form of an expression vector capable of self-replication. In addition, the polynucleotide may be introduced into a host cell in its own form and operably linked to a sequence required for expression in the host cell. As described above, the term "operably linked" may mean that expression control elements (e.g., promoter) and a polynucleotide are functionally linked so that expression control elements can perform transcription control (e.g., transcription initiation) of a polynucleotide encoding a target protein (foreign protein). Operable linking may be performed using a gene recombination technique known in the art, and for example, it may be performed by common site-specific DNA cleavage and ligation, but not limited thereto.

The method for transforming the polynucleotide into a host cell may be performed by any method for introducing nucleic acid into a cell (microorganism), and it may be performed by appropriately selecting a transformation technique known in the art depending on the host cell. As the known transformation method, electroporation, calcium phosphate ($CaPO_4$) precipitation, calcium chloride ($CaCl_2$) precipitation, microinjection, polyethylene glycol (PEG) precipitation (polyethylene glycol-mediated uptake), DEAE-dextran method, cation liposome method, lipofection, lithium acetate-DMSO method, and the like may be exemplified, but not limited thereto.

The introduction (insertion) of the polynucleotide into host cell genome (chromosome) may be performed by appropriately selecting a known method by those skilled in the art, and for example, it may be performed using RNA-guided endonuclease system (or CRISPR system; for example, one or more selected from the group consisting of (a) RNA-guided endonuclease (e.g., Cas9 protein, etc.), encoding gene thereof, or a vector comprising the gene; and (b) guided RNA (e.g., single guide RNA (sgRNA), etc.), encoding DNA thereof, or a mixture comprising the vector comprising DNA (for example, mixture of RNA-guided endonuclease protein and guide RNA, etc.), a complex (for example, ribonucleic acid fusion protein (RNP), a recombinant vector (for example, a vector comprising a RNA-guided endonuclease-encoding gene and guide RNA-encoding DNA together, etc.), and the like), but not limited thereto.

In the present description, the term "vector" means a DNA product containing the nucleotide sequence of the polynucleotide encoding the target protein operably linked to an appropriate regulatory sequence so that a target protein can be expressed in a suitable host. The regulatory sequence may include a promoter capable of initiating transcription, any operator sequence for regulating transcription, a sequence encoding a suitable mRNA ribosome binding site, and/or a sequence for regulating termination of transcription and/or translation. After the vector is transformed into a host cell, it may be expressed independently of the genome of the host cell, or may be integrated into the genome of the host cell.

The vector available in the present description is not particularly limited as long as it is capable of replication in a host cell, and may be selected from all commonly used vectors. Examples of commonly used vectors may include natural or recombinant plasmids, cosmids, viruses, bacteriophages and the like. For example, as the vector, pWE15, M13, MBL3, MBL4, IXII, ASHII, APII, t10, t11, Charon4A, and Charon21A and the like may be used as a phage vector or cosmid vector, and pBR-based, pUC-based, pBluescript II-based, pGEM-based, pTZ-based, pCL-based and pET-based and the like may be used as a plasmid vector, but not limited thereto. Specifically, pDZ, pACYC177, pACYC184, pCL, pECCG117, pUC19, pBR322, pMW118, pCC1BAC vectors, and the like may be exemplified, but not limited thereto.

The vector available in the present description may be a known expression vector and/or a vector for insertion into host cell chromosome of a polynucleotide. The insertion of the polynucleotide into the host cell chromosome may be performed by any method known in the art, for example, homologous recombination or CRISPR system, but not limited thereto. The vector may further comprise a selection marker for confirming whether or not it is inserted into the chromosome. The selection marker is to select cells transformed into a vector, that is, to confirm whether the polynucleotide is inserted, and it may be selected and used among genes conferring a selectable phenotype, such as drug resistance, auxotrophic requirement, resistance to cytotoxic agents, or expression of surface protein. In an environment treated with a selective agent, only cells expressing a selectable marker survive or exhibit other phenotypic characteristics, and thus transformed cells may be selected.

Other example, provides a composition for producing pantothenic acid or pantoic acid, comprising the microorganism.

Other example provides a method for preparation of pantothenic acid or pantoic acid, comprising culturing the microorganism in a medium.

Other example provides a method for increasing pantothenic acid and/or pantoic acid production ability of the microorganism or a method for giving pantothenic acid production ability to the microorganism, comprising enhancing 3-methyl-2-oxobutanoate hydroxymethyltransferase activity of a microorganism.

The enhancing activity of 3-methyl-2-oxobutanoate hydroxymethyltransferase of the microorganism may comprise introducing a mutation so as to express a polypeptide having 3-methyl-2-oxobutanoate hydroxymethyltransferase activity into the microorganism.

The introducing a mutation may comprise introducing (transforming) an encoding polynucleotide of a polypeptide having 3-methyl-2-oxobutanoate hydroxymethyltransferase activity or a recombinant vector comprising the polynucleotide into a microorganism.

Other example provides a method for production of pantothenic acid and/or pantoic acid, comprising culturing the aforementioned microorganism with enhanced activity of 3-methyl-2-oxobutanoate hydroxymethyltransferase in a medium. The method, may further comprise recovering pantothenic acid and/or pantoic acid from the cultured microorganism, medium or both of them, after the culturing.

In the method, the culturing a microorganism is not particularly limited thereto, but may be performed by known batch culturing methods, continuous culturing methods, fed-batch culturing methods, and the like. Then, the culturing condition, is not particularly limited thereto, but may adjust an appropriate pH (For example, pH 5 to 9, specifically, pH 6 to 8, most specifically, pH 6.8) using a basic compound (e.g.: sodium hydroxide, potassium hydroxide or ammonia) or acidic compound (e.g.: phosphate or sulfate), and may maintain an aerobic condition by introducing oxygen or an oxygen-containing gas mixture to the culture. The culturing temperature may be maintained by 20 to 45° C., or 25 to 40° C., and the culturing may be conducted for about 10 to 160 hours, but not limited thereto. The pantothenic acid and/or pantoic acid produced by the culturing may be secreted to the medium or remain in cells.

The medium available for the culturing may use one or more kinds selected from the group consisting of sugar and carbohydrate (e.g.: glucose, sucrose, lactose, fructose, maltose, molasse, starch and cellulose), oil and fat (e.g.: soybean oil, sunflower seed oil, peanut oil and coconut oil), fatty acid (e.g.: palmitic acid, stearic acid and linoleic acid), alcohol (e.g.: glycerol and ethanol), organic acid (e.g.: acetic acid), and the like individually or use them by mixing two or more kinds as a carbon source, but not limited thereto. As a nitrogen source, one or more kinds selected from the group consisting of nitrogen-containing organic compound (e.g.: peptone, yeast extract, meat juice, malt extract, corn steep liquid, soybean meal powder and urea), inorganic compound (e.g.: ammonium sulfate, ammonium chloride, ammonium phosphate, ammonium carbonate and ammonium nitrate), and the like may be used individually, or two or more kinds may be mixed and used, but not limited thereto. As a phosphorus source, one or more kinds selected from the group consisting of potassium dihydrogen phosphate, dipotassium hydrogen phosphate, sodium-containing salts corresponding thereto, and the like may be used individually, or two or more kinds may be mixed and used, but not limited thereto. In addition, the medium may comprise essential growth-promoting substances such as other metal salts (e.g.: magnesium sulfate or iron sulfate), amino acids and/or vitamins, and the like.

The recovering pantothenic acid and/or pantoic acid may collecting desired amino acids from a medium, culture solution or microorganism, using a known appropriate method in the art depending on the culturing method. For example, the recovering may be performed by one or more methods selected from centrifugation, filtration, anion exchange chromatography, crystallization, HPLC, and the like. The method for recovering pantothenic acid and/or pantoic acid may additionally comprise a purification step before that, at the same time, or after that.

Advantageous Effects

In the present description, 3-methyl-2-ketobutanoate hydroxymethyltransferase variant is provided, and a technology for increasing the production ability of pantothenic acid and/or pantoic acid of a microorganism using the same is provided. By introducing a mutation to express the 3-methyl-2-ketobutanoate hydroxymethyltransferase variant into a microorganism, a technology capable of improving the productivity of pantothenic acid and/or pantoic acid or giving the productivity of pantothenic acid and/or pantoic acid is provided.

MODE FOR INVENTION

Hereinafter, the present invention will be more specifically described by examples, but they are illustrative only, and are not intended to limit the scope of the present invention. It is obvious to those skilled in the art that the examples described below may be modified without departing from the essential gist of the invention.

Example 1. 3-Methyl-2-oxobutanoate hydroxymethyltransferase gene search and selection As the result of NCBI BLAST search by setting a gene encoding 3-methyl-2-oxobutanoate hydroxymethyltransferase (panB) of *Corynebacterium glutamicum* ATCC13032 to a query, candidate genes estimated as having activity of the gene encoding 3-methyl-2-oxobutanoate hydroxymethyltransferase and microorganisms having them were selected. Among them, the genes encoding 3-methyl-2-oxobutanoate hydroxymethyltransferase derived from microorganisms having a biosafety level of 1 were selected, and they are summarized in Table 1:

TABLE 1

Primers/plasmids used for selection of microorganisms estimated to have a gene encoding 3-methyl-2-oxobutanoate hydroxymethyltransferase and 3-methyl-2-oxobutanoate hydroxymethyltransferase genes

| | Microorganism name | KCTC Accession No. | Primer | Plasmid |
|---|---|---|---|---|
| 1 | *Escherichia coli* | ATCC47076 | SEQ ID NOs: 1, 2 | pECCG117-panB(EC) |
| 2 | *Bacillus subtilis* | KCTC3135(ATCC 6051) | SEQ ID NOs: 3, 4 | pECCG117-panB(BS) |
| 3 | *Pantoea agglomerans* | KCTC2564(ATCC27155) | SEQ ID NOs: 5, 6 | pECCG117-panB(PA) |
| 4 | *Serratia rubidaea* | KCTC2927(ATCC27593) | SEQ ID NOs: 7, 8 | pECCG117-panB(SR) |
| 5 | *Serratia proteamaculans* | KCTC2936(ATCC19323) | SEQ ID NOs: 9, 10 | pECCG117-panB(SP) |
| 6 | *Pseudomonas resinovorans* | KCTC12498(ATCC14235) | SEQ ID NOs: 11, 12 | pECCG117-panB(PR) |
| 7 | *Pedobacter terrae* | KCTC12762(DSM17933) | SEQ ID NOs: 13, 14 | pECCG117-panB(PT) |
| 8 | *Citrobacter bitternis* | KCTC42139(JCM30009) | SEQ ID NOs: 15, 16 | pECCG117-panB(CB) |
| 9 | *Enterobacter cloacae* | KCTC2519(ATCC23355) | SEQ ID NOs: 17, 18 | pECCG117-panB(ECl) |
| 10 | *Achromobacter piechaudii* | KCTC22890(ATCC43552) | SEQ ID NOs: 19, 20 | pECCG117-panB(AP) |
| 11 | *Staphylococcus epidermidis* | KCTC1917(ATCC12228) | SEQ ID NOs: 21, 22 | pECCG117-panB(SE) |
| 12 | *Shigella flexneri* | KCTC12073 | SEQ ID NOs: 23, 24 | pECCG117-panB(SF) |
| 13 | *Corynebacterium glutamicum* | KCTC9097(ATCC13032) | SEQ ID NOs: 25, 26 | pECCG117-panB(CG) |

Example 2. Production of the Genus *Corynebacterium* Microorganism in which Foreign Microorganism-Derived 3-Methyl-2-Oxobutanoate Hydroxymethyltransferase After extracting genome of the microorganisms secured in Example 1, PCR was performed using the primer sequences of Table 1 using it as a template, and DNA fragments encoding 3-methyl-2-oxobutanoate hydroxymethyltransferase were amplified. The PCR was performed using PfuUltra™ high-confidence DNA polymerase (Stratagene), and was performed under the condition of repeating denaturation at 95° C. for 30 seconds; annealing at 55° C. for 30 seconds; and polymerization at 72° C. for 1 minute 30 times. As a result, DNA fragments encoding each 3-methyl-2-oxobutanoate hydroxymethyltransferase (panB) were obtained.

In order to secure *Corynebacterium glutamicum*-derived PLM1 promoter, PCR was performed using primers of SEQ ID NOs: 27 and 28 using *Corynebacterium glutamicum* (ATCC13032) genome as a template as same as described above to obtain promoter DNA fragments.

After treating with restriction enzyme BamHI, by cloning pECCG117 vector heat-treated at 65° C. for 20 minutes (Korean Patent No. 10-0057684) and obtained DNA fragments (each panB, PLM1 promoter) to be a molarity (M) of 2:1:1 (pECCG117 vector: panB: PLM1) according to the provided manual using Infusion Cloning Kit of TakaRa, plasmids were obtained, and the names of the obtained plasmids and introduced gene information were marked in Table 1 above.

By transforming the produced 13 kinds of vectors into *Corynebacterium glutamicum* ATCC13032 by electroporation, strains expressing foreign PanB (3-methyl-2-oxobutanoate hydroxymethyltransferase) were produced.

Example 3. Investigation of pantothenic acid production ability of the genus *Corynebacterium* microorganism in which foreign microorganism-derived 3-methyl-2-oxobutanoate hydroxymethyltransferase is expressed In order to confirm the productivity of pantothenic acid of various foreign microorganism-derived panB expressing strains obtained in Example 2, a parent strain (non-transformed strain) and the strains were inoculated into a 250 ml corner-baffle flask containing production medium 25 ml consisting of the following composition, respectively, and then cultured with shaking at 200 rpm at 32° C. for 48 hours to prepare pantothenic acid.

<Production Medium>

Glucose 10%, beta-alanine 0.5%, yeast extract 0.4%, ammonium sulfate 1.5%, potassium phosphate monobasic 0.1%, magnesium sulfate 7 hydrate 0.05%, iron sulfate 7 hydrate 10 mg/l, manganese sulfate 1 hydrate 6.7 mg/l, biotin 50 μg/l, thiamine·HCl 100 μg/l, pH 7.2

The obtained culture solution was centrifuged at 20,000 rcf for 10 minutes, and then the supernatant was diluted by 1/10 with TDW (triple distilled water), and then HPLC analysis was performed to measure the concentration of pantothenic acid and L-valine, and the result was shown in Table 2 below.

TABLE 2

| | Pantothenic acid concentration (g/L) | L-valine concentration (g/L) |
|---|---|---|
| ATCC13032 (wild type) | 0.0 | 2.4 |
| ATCC13032 pECCG117-panB(EC) | 1.2 | 1.5 |

TABLE 2-continued

| | Pantothenic acid concentration (g/L) | L-valine concentration (g/L) |
|---|---|---|
| ATCC13032 pECCG117-panB(BS) | 0.5 | 1.9 |
| ATCC13032 pECCG117-panB(PA) | 0.6 | 2.0 |
| ATCC13032 pECCG117-panB(SR) | 0.7 | 1.8 |
| ATCC13032 pECCG117-panB(SP) | 0.3 | 2.2 |
| ATCC13032 pECCG117-panB(PR) | 0.7 | 1.9 |
| ATCC13032 pECCG117-panB(PT) | 0.7 | 2.0 |
| ATCC13032 pECCG117-panB(CB) | 0.7 | 2.0 |
| ATCC13032 pECCG117-panB(ECl) | 0.6 | 2.1 |
| ATCC13032 pECCG117-panB(AP) | 0.6 | 1.9 |
| ATCC13032 pECCG117-panB(SE) | 0.5 | 2.0 |
| ATCC13032 pECCG117-panB(SF) | 0.7 | 1.9 |
| ATCC13032 pECCG117-panB(CG) | 0.6 | 2.0 |

As shown in Table 2, the parent strain, *Corynebacterium glutamicum* ATCC 13032 did not produce pantothenic acid, whereas all the tested *Corynebacterium glutamicum* strains expressing foreign microorganism-derived panB produced about 0.6 g/L pantothenic acid. In particular, among the foreign microorganism-derived PanB expressing strains, *E. coli*-derived panB expressing strain, ATCC13032 pECCG117-panB (EC) showed the highest pantothenic acid productivity (1.2 g/L).

The above result showed that 13 kinds of microorganism-derived enzymes (3-methyl-2-oxobutanoate hydroxymethyltransferase) selected in Example 1 showed the pantothenic acid production ability, and among them, the *E. coli*-derived enzyme showed especially high pantothenic acid production ability.

Example 4. Production of the genus *Corynebacterium* microorganism in which *E. coli*-derived 3-methyl-2-oxobutanoate hydroxymethyltransferase gene is introduced A plasmid to introduce the *E. coli*-derived 3-methyl-2-oxobutanoate hydroxymethyltransferase-encoding gene (panB) determined as having the especially excellent pantothenic acid production ability in Example 3 into *Corynebacterium glutamicum* ATCC13032 was produced.

At first, a vector to delete panB present in the parent strain was produced. PCR was performed using primers of SEQ ID NOs: 29 and 30 and SEQ ID NOs: 31 and 32 using the genome DNA of *Corynebacterium glutamicum* ATCC13032 as a template. PCR was performed under the condition of repeating denaturation at 95° C. for 30 seconds; annealing at 55° C. for 30 seconds; and polymerization at 72° C. for 1 minute 25 times. As a result, gene fragments of 1000 bp at the top region of the panB gene and 1000 bp at the bottom region of the panB gene were obtained, respectively, and each amplified product was purified using PCR Purification kit of QIAGEN and was used as insertion DNA fragments for vector production.

After treating with restriction enzyme smaI, by cloning pDZ vector heat-treated at 65° C. for 20 minutes (Korean Patent No. 0924065) and DNA fragments (gene fragments of 1000 bp at the top region of panB gene and gene fragments of 1000 bp at the bottom region of panB gene) to be a molarity (M) of 2:1:1 according to the provided manual using Infusion Cloning Kit of TakaRa, a vector to delete panB gene on chromosome, pDZ_ΔpanB was produced.

In order to prepare *E. coli*-derived panB gene, PCR was performed using primers of SEQ ID NOs: 33 and 34 using the plasmid pECCG117-panB (EC) produced in Example 2 as a template. PCR was performed by repeating denaturation at 95° C. for 30 seconds; annealing at 55° C. for 30 seconds; and polymerization at 72° C. for 1 minute 25 times, and as a result, DNA fragments of 1077 bp were obtained. After treating with restriction enzyme smaI, by cloning pDZ_ΔpanB vector heat-treated at 65° C. for 20 minutes and the obtained DNA fragments to be a molarity (M) of 1:2 according to the provided manual using Infusion Cloning Kit of TakaRa, a vector to introduce *E. coli*-derived panB gene on chromosome, pDZ_ΔpanB::PLM1-panB (EC) was produced.

The produced vectors, pDZ_ΔpanB and pDZ_ΔpanB::panB (EC) were transformed into *Corynebacterium glutamicum* ATCC13032, respectively, by electroporation, and through a secondary cross process, a strain in which panB was deleted (ΔpanB strain) and a strain in which *E. coli*-derived panB was introduced (ΔpanB::panB (EC)) were obtained on chromosome, respectively. Whether or not the appropriate substitution of *E. coli*-derived panB was confirmed using the following primer combination using MASA (Mutant Allele Specific Amplification) PCR technique (Takeda et al., Hum. Mutation, 2, 112-117 (1993)). In other words, primary determination was made by selecting strains amplified in the primer combination corresponding to *E. coli* panB (SEQ ID NOs: 35 and 28 and SEQ ID NOs: 36 and 1), and secondary confirmation was conducted by analyzing the panB sequence of the selected strain using the primer combination of SEQ ID NO: 35 and SEQ ID NO: 36.

In order to confirm the pantothenic acid productivity of the mutant strains obtained as described above, after inoculating *Corynebacterium glutamicum* ATCC 13032 wild type strain, ΔpanB strain, and ΔpanB::panB (EC) mutant strain into a 250 ml corner-baffle flask containing production medium (see Example 3) 25 ml, they were cultured with shaking at 300 rpm at 32° C. for 48 hours to prepare pantothenic acid.

The obtained culture solution was centrifuged at 20,000 rcf for 10 minutes, and then the supernatant was diluted by 1/10 with TDW (triple distilled water), and then HPLC analysis was performed to measure the concentration of pantothenic acid and L-valine, and the result was shown in Table 3 below.

TABLE 3

| | Pantothenic acid concentration (g/L) | L-valine concentration (g/L) |
|---|---|---|
| ATCC13032 (wild type) | 0.1 | 1.9 |
| ATCC13032 ΔpanB | 0.0 | 2.7 |
| ATCC13032 ΔpanB::panB(EC) | 0.4 | 1.3 |

As shown in Table 3, the *Corynebacterium glutamicum* ATCC 13032 wild type and panB deleted (ΔpanB) strain did not produce pantothenic acid at all or hardly produced it, whereas the mutant *Corynebacterium glutamicum* expressing foreign panB (ΔpanB::panB (EC)) produced pantothenic acid at a concentration of 0.4 g/l.

Example 5. Random Mutant Strain Production Through Artificial Mutation (NTG-Based Mutation) and panB Producing Strain Selection In the present example, in order to obtain a microorganism mutant strain with much more enhanced production ability of pantothenic acid, using the following method, a mutation of the microorganism was induced using the mutant *Corynebacterium glutamicum* ATCC13032 ΔpanB::panB (EC) strain expressing *E. coli*-derived panB produced according to Example 4 as a parent strain.

Specifically, the *Corynebacterium glutamicum* ATCC13032 ΔpanB::panB (EC) strain was activated by culturing it in an activation medium for 16 hours, and was inoculated in a seed medium sterilized at 121° C. for 15 minutes and cultured for 14 hours, and then the culture solution 5 ml was recovered. After washing the recovered culture solution with 100 mM citric buffer, NTG (N-Methyl-N'-nitro-N-nitrosoguanidine) was added so as to be the final concentration of 200 mg/l and was treated for 20 minutes, and was washed with 100 mM phosphate buffer. As the result of measuring the death rate by smearing the NTG-treated strain to a minimal medium, the death rate was shown as 85%. The survived cells were inoculated and cultured, and finally, 2 kinds of mutant strains showing the excellent pantothenic acid production ability were selected and named *Corynebacterium glutamicum* CJVB5-01 and CJVB5-02 (*Corynebacterium glutamicum*, CJVB5-02).

The composition of the medium used in the present example was as follows.

<Activation Medium>

Beef extract 1%, polypeptone 1%, sodium chloride 0.5%, yeast extract 1%, agar 2%, pH 7.2

<Production Medium>

Glucose 10%, beta-alanine 0.5%, yeast extract 0.4%, ammonium sulfate 1.5%, potassium phosphate monobasic 0.1%, magnesium sulfate 7 hydrate 0.05%, iron sulfate 7 hydrate 10 mg/l, manganese sulfate 1 hydrate 6.7 mg/l, biotin 50 μg/l, thiamine·HCl 100 g/l, pH 7.2

<Minimal Medium>

Glucose 1.0%, ammonium sulfate 0.4%, magnesium sulfate 0.04%, potassium phosphate monobasic 0.1%, urea 0.1%, thiamine 0.001%, biotin 200 μg/l, agar 2%, pH 7.2

In order to confirm the pantothenic acid production ability of the obtained mutant strains *Corynebacterium glutamicum* CJVB5-01 and CJVB5-02, after inoculating *Corynebacterium glutamicum* ATCC13032 ΔpanB::panB (EC) strain, CJVB5-01 mutant strain and CJVB5-02 mutant strain into a 250 ml corner-baffle flask containing production medium 25 ml, respectively, they were cultured with shaking at 200 rpm at 32° C. for 48 hours to prepare pantothenic acid.

The obtained culture solution was centrifuged at 20,000 rcf for 10 minutes, and then the supernatant was diluted by 1/10 with TDW (triple distilled water), and then HPLC analysis was performed to measure the concentration of pantothenic acid and L-valine, and the result was shown in Table 4 and Table 5 below.

TABLE 4

| | Pantothenic acid concentration (g/L) | L-valine concentration (g/L) |
|---|---|---|
| ATCC13032 ΔpanB | 0.0 | 2.4 |
| ATCC13032 ΔpanB::panB(EC) | 0.3 | 1.4 |
| CJVB5-01 | 1.2 | 1.0 |

TABLE 5

| | Pantothenic acid concentration (g/L) | L-valine concentration (g/L) |
|---|---|---|
| ATCC13032 ΔpanB::panB(EC) | 0.3 | 0.9 |
| CJVB5-02 | 1.7 | 0.2 |

As shown in Table 4 and Table 5 above, it was confirmed that *Corynebacterium glutamicum* ΔpanB strain did not produce pantothenic acid, and the *Corynebacterium glutamicum* CJVB5-01 mutant strain and CJVB5-02 mutant strain showed more excellent pantothenic acid production ability, compared to the foreign panB-inserted *Corynebacterium glutamicum* ΔpanB::panB (EC). In addition, it could be confirmed that the pantothenic acid production ability of the CJVB5-1 mutant strain and CJVB5-02 mutant strain was much stronger than that of the wild type, considering that the concentration of valine, a substance using 3-methyl-2-oxobutanoate as a substrate decreased.

As the result of genome sequencing of the *Corynebacterium glutamicum* CJVB5-01 mutant strain, it was confirmed that the inserted *E. coli* panB gene was mutated to encode a variant in which G116A mutation (substitution of the 116th amino acid residue in the amino acid sequence of SEQ ID NO: 37, G (Gly) with A (Ala)) was introduced into wild type *E. coli* 3-methyl-2-oxobutanoate hydroxymethyltransferase (SEQ ID NO: 37). Hereinafter, the indication of amino acid mutations using amino acid positions such as 'G116A' is understood to mean amino acid mutations and/or genetic mutations inducing such amino acid mutations. The amino acid sequence of of the *E. coli* 3-methyl-2-oxobutanoate hydroxymethyltransferase variant in which the G116A mutation was introduced was shown in SEQ ID NO: 62.

As the result of genome sequencing of the *Corynebacterium glutamicum* CJVB5-02 mutant strain, it was confirmed that the inserted *E. coli* panB gene was mutated to encode a variant in which A159L mutation (substitution of the 159th amino acid residue in the amino acid sequence of SEQ ID NO: 37, A (Ala, alanine) with L (Leu, leucine)) was introduced into wild type *E. coli* 3-methyl-2-oxobutanoate hydroxymethyltransferase (SEQ ID NO: 37). Hereinafter, the indication of amino acid mutations using amino acid positions such as 'A159L' is understood to mean amino acid mutations and/or genetic mutations inducing such amino acid mutations. The amino acid sequence of the *E. coli* 3-methyl-2-oxobutanoate hydroxymethyltransferase variant in which the A159L mutation was introduced was shown in SEQ ID NO: 110.

As a result, it was confirmed that the CJVB5-01 mutant strain and CJVB5-02 mutant strain produced pantothenic acid with high efficiency and high yield, without inhibiting a pathway of synthesizing pantothenic acid from pyruvic acid.

Example 6. Production of mutant panB plasmid having 3-methyl-2ketobutanoate hydroxymethyltransferase activity In order to confirm that the amino acid residues corresponding to the 116th and/or 159th residues, positions of mutations of *E. coli* PanB (3-methyl-2-oxobutanoate hydroxymethyltransferase) confirmed as affecting the pantothenic acid production ability through Example 5 were important positions, a mutant in which amino acid residues at these positions were substituted with other amino acids was produced and the effect was confirmed.

Using primers described in Table 6 below using pECCG117-panB (EC) produced in Example 2 (See Table 1) as a template, a variant in which random mutagenesis (saturated mutagenesis) in which the amino acid at the 116th position of *E. coli* PanB (SEQ ID NO: 37), G (Gly) was substituted with another amino acid was introduced (that is, the panB gene mutated to encode *E. coli* PanB in which the random mutagenesis was introduced was introduced) was produced. In addition, using primers described in Table 7 below, a variant, in which random mutagenesis in which the amino acid at the 159th position of *E. coli* PanB (SEQ ID NO: 37), A (Ala) was substituted with another amino acid was introduced, was produced. The pECCG117-panB (EC) produced in Example 1 was used as a template. The amino acids substituted according to the mutant of the mutant strain in which each saturated mutagenesis was introduced and primers used for each mutant were summarized in Table 6 and Table 7 below:

TABLE 6

| Template | Amino acid substitution | Used primer |
|---|---|---|
| pECCG117-panB(EC) | G116S | SEQ ID NOs: 27, 38/39, 28 |
| | G116C | SEQ ID NOs: 27, 40/41, 28 |
| | G116L | SEQ ID NOs: 27, 42/43, 28 |
| | G116I | SEQ ID NOs: 27, 44/45, 28 |
| | G116T | SEQ ID NOs: 27, 46/47, 28 |
| | G116V | SEQ ID NOs: 27, 48/49, 28 |
| | G116M | SEQ ID NOs: 27, 50/51, 28 |
| | G116D | SEQ ID NOs: 27, 52/53, 28 |
| | G116E | SEQ ID NOs: 27, 54/55, 28 |
| | G116N | SEQ ID NOs: 27, 56/57, 28 |
| | G116Q | SEQ ID NOs: 27, 58/59, 28 |
| | G116A | SEQ ID NOs: 27, 60/61, 28 |

TABLE 7

| Template | Substituted amino acid | Used primer |
|---|---|---|
| pECCG117-panB(EC) | A159R | SEQ ID NOs: 74, 75/76, 77 |
| | A159S | SEQ ID NOs: 74, 78/79, 77 |
| | A159Y | SEQ ID NOs: 74, 80/81, 77 |
| | A159C | SEQ ID NOs: 74, 82/83, 77 |
| | A159P | SEQ ID NOs: 74, 84/85, 77 |
| | A159H | SEQ ID NOs: 74, 86/87, 77 |
| | A159L | SEQ ID NOs: 74, 88/89, 77 |
| | A159I | SEQ ID NOs: 74, 90/91, 77 |
| | A159T | SEQ ID NOs: 74, 92/93, 77 |
| | A159K | SEQ ID NOs: 74, 94/95, 77 |
| | A159V | SEQ ID NOs: 74, 96/97, 77 |
| | A159M | SEQ ID NOs: 74, 98/99, 77 |
| | A159D | SEQ ID NOs: 74, 100/101, 77 |
| | A159E | SEQ ID NOs: 74, 102/103, 77 |
| | A159N | SEQ ID NOs: 74, 104/105, 77 |
| | A159Q | SEQ ID NOs: 74, 106/107, 77 |
| | WT (SEQ ID NO: 37) | SEQ ID NOs: 74, 77 |

Specifically, using primers presented in Table 6 and Table 7 above, PCR was performed using pECCG117-panB (EC) (See Table 1) produced in Example 2 as a template. As polymerase, Solg™ Pfu-X DNA polymerase (SolGent co., Ltd.) was used, and PCR was progressed by denaturing at 95° C. for 10 minutes, and then repeating denaturation at 95° C. for 30 seconds, annealing at 55° C. for 30 seconds and polymerization at 72° C. for 1 minute 25 times, and then performing polymerization at 72° C. for 5 minutes. As a result, 610 bp DNA fragments at the 5' upstream region and 470 bp DNA fragments at the 3' downstream region centering on the mutation (116th residue) of 3-methyl-2-oxobutanoate hydroxymethyltransferase gene were obtained, and 477 bp DNA fragments at the 5' upstream region and 318 bp DNA fragments at the 3' downstream region centering on the 159th residue were obtained.

After treating with restriction enzyme BamHI, by cloning pECCG117 vector heat-treated at 65° C. for 20 minutes (Korean Patent No. 10-0057684) and obtained each DNA fragment (116th residue: 610 bp DNA fragments at the 5' upstream region and 470 bp DNA fragments at the 3' downstream region, 159th residue: 477 bp DNA fragments at the 5' upstream region and 318 bp DNA fragments at the 3' downstream region) to be a molarity (M) of 2:1:1 according to the provided manual using Infusion Cloning Kit of TakaRa, a plasmid for mutant panB introduction was obtained. In order to secure *Corynebacterium glutamicum*-derived PLM1 promoter, PCR was performed using *Corynebacterium glutamicum* (ATCC13032) genome DNA as a template using primers of SEQ ID NOs: 108 and 109 as same as described above, to obtain promoter DNA fragments.

The information of the obtained mutant plasmids was summarized in Table 8 and Table 9 below:

TABLE 8

| Mutation position | Amino acid substitution | Mutant plasmid produced to induce amino acid substitution |
|---|---|---|
| Amino acid residue corresponding to the 116th residue of Wild type panB (SEQ ID NO: 37) | G116S | pECCG117-panB(G116S) |
| | G116C | pECCG117-panB(G116C) |
| | G116L | pECCG117-panB(G116L) |
| | G116I | pECCG117-panB(G116I) |
| | G116T | pECCG117-panB(G116T) |
| | G116V | pECCG117-panB(G116V) |
| | G116M | pECCG117-panB(G116M) |
| | G116D | pECCG117-panB(G116D) |
| | G116E | pECCG117-panB(G116E) |
| | G116N | pECCG117-panB(G116N) |
| | G116Q | pECCG117-panB(G116Q) |
| | G116A | pECCG117-panB(G116A) |

TABLE 9

| Mutation position | Amino acid substitution | Mutant plasmid produced to induce amino acid substitution |
|---|---|---|
| Amino acid residue corresponding to the 116th residue of Wild type panB (SEQ ID NO: 37) | A159R | pECCG117-panB(A159R) |
| | A159S | pECCG117-panB(A159S) |
| | A159Y | pECCG117-panB(A159Y) |
| | A159C | pECCG117-panB(A159C) |
| | A159P | pECCG117-panB(A159P) |
| | A159H | pECCG117-panB(A159H) |
| | A159L | pECCG117-panB(A159L) |
| | A159I | pECCG117-panB(A159I) |
| | A159T | pECCG117-panB(A159T) |
| | A159K | pECCG117-panB(A159K) |
| | A159V | pECCG117-panB(A159V) |
| | A159M | pECCG117-panB(A159M) |
| | A159D | pECCG117-panB(A159D) |
| | A159E | pECCG117-panB(A159E) |
| | A159N | pECCG117-panB(A159N) |
| | A159Q | pECCG117-panB(A159Q) |
| | WT | pECCG117-panB(WT) |

Example 7. Evaluation of pantothenic acid production ability of 3-methyl-2ketobutanoate hydroxymethyltransferase The mutant plasmid produced in Example 6 (Table 8 and Table 9) and pECCG117-panB (WT-EC) (Table 1) were introduced into the ATCC13032 ΔpanB strain produced in Example 4 by an electric pulse method, and then they were smeared in a selective medium containing kanamycin 25 mg/l to obtain total 19 kinds of transformed mutant strains in which each random mutagenesis (saturated mutagenesis) was introduced. Then, by progressing flask evaluation by the same method as Example 3, the production ability of the obtained pantothenic acid was measured. The obtained result was shown in Table 10 and Table 11:

TABLE 10

| Strain | Pantothenic acid (g/L) | | | |
|---|---|---|---|---|
| | Arrangement 1 | Arrangement 2 | Arrangement 3 | Average |
| ATCC 13032 ΔpanB (Control group) | 0.0 | 0.0 | 0.0 | 0.0 |
| ATCC 13032 ΔpanB pECCG117-panB(G116S) | 1.5 | 1.9 | 1.6 | 1.7 |
| ATCC 13032 ΔpanB pECCG117-panB(G116C) | 1.2 | 1.3 | 1.2 | 1.2 |
| ATCC 13032 ΔpanB pECCG117-panB(G116L) | 1.6 | 1.5 | 1.4 | 1.5 |
| ATCC 13032 ΔpanB pECCG117-panB(G116I) | 1.5 | 1.7 | 1.6 | 1.6 |
| ATCC 13032 ΔpanB pECCG117-panB(G116T) | 2.4 | 2.5 | 2.3 | 2.4 |
| ATCC 13032 ΔpanB pECCG117-panB(G116V) | 1.6 | 1.7 | 1.4 | 1.6 |
| ATCC 13032 ΔpanB pECCG117-panB(G116M) | 0.9 | 0.9 | 1.1 | 1.0 |
| ATCC 13032 ΔpanB pECCG117-panB(G116D) | 1.3 | 1.1 | 1.2 | 1.2 |
| ATCC 13032 ΔpanB pECCG117-panB(G116E) | 1.9 | 1.2 | 2.1 | 1.7 |
| ATCC 13032 ΔpanB pECCG117-panB(G116N) | 2.5 | 2.5 | 2.6 | 2.5 |
| ATCC 13032 ΔpanB pECCG117-panB(G116Q) | 1.0 | 1.1 | 1.0 | 1.0 |
| ATCC 13032 ΔpanB pECCG117-panB(G116A) | 2.6 | 2.9 | 2.9 | 2.8 |
| ATCC 13032 ΔpanB pECCG117-panB(WT) | 0.9 | 0.8 | 1.0 | 0.9 |

As could be seen in Table 10 above, the ATCC13032 ΔpanB strain did not produce pantothenic acid, whereas all the *E. coli* PanB (wild type) or mutant strains in which its mutant was introduced showed the pantothenic acid production ability. In addition, the mutant strains in which the G116S, G116C, G116L, G116I, G116T, G116V, G116D, G116E, G116N, G116A, G116M, or G116Q mutation was introduced produced pantothenic acid at a much higher level compared to ATCC 13032 ΔpanB pECCG117-panB (WT) which was the mutant strain comprising the *E. coli* PanB (wild type). As a result, both the wild type of *E. coli* PanB and mutant had the effect of increasing pantothenic acid production, and in particular, it could be confirmed that the 116th amino acid residue of PanB (SEQ ID NO: 37) was the important position for pantothenic acid production, and when the amino acid at this position was substituted with various amino acids different from the original one, the production ability of pantothenic acid was further increased.

The ATCC 13032 ΔpanB pECCG117-panB (G116A) strain (named *Corynebacterium glutamicum* CV03-5001) confirmed as having the most excellent production ability of pantothenic acid in the present example was deposited to Korean Culture Center of Microorganisms located in Hongje-dong, Seodaemun-gu, Seoul, Korea on Jun. 8, 2020 and was given an accession number of KCCM12744P.

TABLE 11

Pantothenic acid production ability of saturated mutagenesis-introduced strain

| Strain | Pantothenic acid (g/L) | | | |
|---|---|---|---|---|
| | Arrangement 1 | Arrangement 2 | Arrangement 3 | Average |
| ATCC 13032 | 0.0 | 0.0 | 0.0 | 0 |
| ATCC 13032 pECCG117-panB(A159R) | 0.7 | 0.8 | 0.8 | 0.77 |
| ATCC 13032 pECCG117-panB(A159S) | 2.5 | 2.9 | 2.6 | 2.67 |
| ATCC 13032 pECCG117-panB(A159Y) | 0.8 | 0.7 | 0.8 | 0.77 |
| ATCC 13032 pECCG117-panB(A159C) | 2.2 | 2.3 | 2.2 | 2.23 |
| ATCC 13032 pECCG117-panB(A159P) | 1.2 | 1.3 | 1.3 | 1.27 |
| ATCC 13032 pECCG117-panB(A159H) | 0.7 | 0.8 | 0.7 | 0.73 |
| ATCC 13032 pECCG117-panB(A159L) | 2.8 | 3.1 | 2.9 | 2.93 |
| ATCC 13032 pECCG117-panB(A159I) | 2.5 | 2.7 | 2.6 | 2.6 |

TABLE 11-continued

| Pantothenic acid production ability of saturated mutagenesis-introduced strain | | | | |
|---|---|---|---|---|
| | Pantothenic acid (g/L) | | | |
| Strain | Arrangement 1 | Arrangement 2 | Arrangement 3 | Average |
| ATCC 13032 pECCG117-panB(A159T) | 2.1 | 2.1 | 2.3 | 2.17 |
| ATCC 13032 pECCG117-panB(A159K) | 0.9 | 0.6 | 0.7 | 0.73 |
| ATCC 13032 pECCG117-panB(A159V) | 2.6 | 2.7 | 2.4 | 2.57 |
| ATCC 13032 pECCG117-panB(A159M) | 1.9 | 1.9 | 2.2 | 2 |
| ATCC 13032 pECCG117-panB(A159D) | 1.3 | 1.1 | 1.2 | 1.2 |
| ATCC 13032 pECCG117-panB(A159E) | 0.8 | 0.8 | 0.7 | 0.77 |
| ATCC 13032 pECCG117-panB(A159N) | 1.2 | 1.5 | 1.6 | 1.43 |
| ATCC 13032 pECCG117-panB(A159Q) | 1.2 | 1.1 | 1.2 | 1.17 |
| ATCC 13032 pECCG117-panB(WT) | 0.7 | 0.7 | 0.7 | 0.7 |

In addition, as could be confirmed in Table 11 above, the wild type *Corynebacterium glutamicum* ATCC 13032 strain did not produce pantothenic acid, whereas all the 19 kinds of mutant strains produced above showed the pantothenic acid production ability, and among them, the mutant strain in which the amino acid corresponding to the 159th residue of the wild type panB (SEQ ID NO: 37) was mutated into arginine (R), serine(S), tyrosine (Y), cysteine (C), proline (P), histidine (H), leucine (L), isoleucine (I), threonine (T), lysine (K), valine (V), methionine (M), aspartic acid (D), glutamic acid (E), asparagine (N), or glutamine (Q), produced pantothenic acid at a high level, compared to the ATCC 13032 pECCG117-panB (WT) strain comprising the wild type panB. As a result, it could be confirmed that the amino acid residue corresponding to the 159th residue of panB (SEQ ID NO: 37) was the important position for pantothenic acid production, and it could be confirmed that when the amino acid at this position was substituted with various amino acids different from the original one, the production ability of pantothenic acid was further increased.

The ATCC 13032 ΔpanB pECCG117-panB (A159L) strain confirmed as having the most excellent production ability of pantothenic acid in the present example was named was CV03-5002 and was deposited to Korean Culture Center of Microorganisms located in Hongje-dong, Seodaemun-gu, Seoul, Korea on Apr. 13, 2021 and was given an accession number of KCCM12973P.

Example 8. Production and evaluation of mutant 3-methyl-2ketobutanoate hydroxymethyltransferase with enhanced pantothenic acid production ability It was confirmed whether there was an additional activity improvement by combining the 3-methyl-2ketobutanoate hydroxymethyltransferase G116A variant and the 3-methyl-2ketobutanoate hydroxymethyltransferase A159L variant of which effect was confirmed in Example 7.

To produce a vector comprising the G116A and A159L variants, a vector comprising both G116A and A159L was produced using primers of SEQ ID NOs: 74, 126 and SEQ ID NOs: 77, 127 using pECCG117-panB (A159L) produced in Example 2 as a template in the same way as described in Example 2. The produced mutant plasmid pECCG117-panB (G116A, A159L) was introduced into the wild type *Corynebacterium glutamicum* ATCC13032 strain by an electric pulse method, and then was smeared into a selective medium containing kanamycin 25 mg/L to obtain each transformed strain. Then, by progressing flask evaluation by the same method as Example 2, the production ability of the obtained pantothenic acid was measured. The obtained result was shown in Table 12 below.

TABLE 12

| Pantothenic acid production ability of mutant strain comprising G116A and A159L | | | | |
|---|---|---|---|---|
| | Pantothenic acid (g/L) | | | |
| Strain | Arrangement 1 | Arrangement 2 | Arrangement 3 | Average |
| ATCC 13032 | 0.0 | 0.0 | 0.0 | 0 |
| ATCC 13032 pECCG117-panB(WT) | 0.7 | 0.7 | 0.6 | 0.67 |
| ATCC 13032 pECCG117-panB(A159L) | 2.9 | 2.8 | 3.1 | 2.93 |
| ATCC 13032 pECCG117-panB(G116A) | 2.2 | 2.4 | 2.1 | 2.23 |
| ATCC 13032 pECCG117-panB(G116A, A159L) | 3.9 | 3.7 | 3.7 | 3.77 |

As could be confirmed in Table 12 above, the ATCC 13032 strain did not produce pantothenic acid, whereas the mutant strain comprising all the amino acid mutation corresponding to the 116th residue of panB and the amino acid mutation corresponding to the 159th residue produced pantothenic acid at a higher level compared to the ATCC 13032 pECCG117-panB (WT) strain comprising the wild type panB, and produced pantothenic acid at a higher level even than the mutant strains comprising an A159L or G116A mutation. As a result, it could be confirmed that the amino acids corresponding to the 116th and 159th residues of panB were important positions for pantothenic acid production, and it could be confirmed that when the amino acids at these positions were substituted with amino acids different from the original one, the production ability of pantothenic acid was further increased.

From the above description, those skilled in the art to which the present application pertains will be able to understand that the present application may be embodied in other specific forms without changing the technical spirit or essential characteristics thereof. In this regard, it should be understood that the examples described above are illustrative in all respects and not limitative. The scope of the present application should be construed as including all changes or modifications derived from the meaning and scope of the claims to be described below and equivalent concepts rather than the detailed description above, in the scope of the present application.

[Accession Number]

Depository authority name: Korean Culture Center of Microorganisms
Accession number: KCCM12744P
Accession date: 20200608
Depository authority name: Korean Culture Center of Microorganisms
Accession number: KCCM12973P
Accession date: 20210413

The invention claimed is:

1. A polypeptide comprising an amino acid sequence having at least 95% sequence identity to SEQ ID NO: 37, wherein the amino acid at the position corresponding to position 159 of the polypeptide of SEQ ID NO: 37 is substituted with another amino acid, wherein the polypeptide has 3-methyl-2-oxobutanoate hydroxymethyltransferase activity.

2. The polypeptide according to claim 1, wherein the amino acid at the position corresponding to position 159 of the polypeptide of SEQ ID NO: 37 is substituted with arginine (R), serine(S), tyrosine (Y), cysteine (C), proline (P), histidine (H), leucine (L), isoleucine (I), threonine (T), lysine (K), valine (V), methionine (M), aspartic acid (D), glutamic acid (E), asparagine (N), or glutamine (Q).

3. The polypeptide according to claim 1, wherein the polypeptide comprises an amino acid sequence selected from the group consisting of SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124 and SEQ ID NO: 125.

4. The polypeptide according to claim 1, wherein the amino acid at the position corresponding to position 116 of the polypeptide of SEQ ID NO: 37 is substituted with another amino acid.

5. The polypeptide according to claim 4, wherein the amino acid at the position corresponding to position 116 of the polypeptide of SEQ ID NO: 37 is substituted with alanine (A), asparagine (N), threonine (T), glutamic acid (E), serine(S), valine (V), isoleucine (I), leucine (L), aspartic acid (D), cysteine (C), glutamine (Q), or methionine (M).

6. The polypeptide according to claim 4, wherein the polypeptide comprises the amino acid sequence of SEQ ID NO: 128.

* * * * *

SEQUENCE LISTING

```
<160> NUMBER OF SEQ ID NOS: 128

<210> SEQ ID NO 1
<211> LENGTH: 37
<212> TYPE: DNA
<213> ORGANISM: Artificial Sequence
<220> FEATURE:
<223> OTHER INFORMATION: synthetic_primer

<400> SEQUENCE: 1

tagatcgaaa ggtgcacaaa gatgaaaccg accacca                              37


<210> SEQ ID NO 2
<211> LENGTH: 41
<212> TYPE: DNA
<213> ORGANISM: Artificial Sequence
<220> FEATURE:
<223> OTHER INFORMATION: synthetic_primer

<400> SEQUENCE: 2

ccgctctaga actagtggat cttaatggaa actgtgttct t                         41


<210> SEQ ID NO 3
<211> LENGTH: 36
<212> TYPE: DNA
<213> ORGANISM: Artificial Sequence
<220> FEATURE:
<223> OTHER INFORMATION: synthetic_primer

<400> SEQUENCE: 3

tagatcgaaa ggtgcacaaa gatgaaaccg accacc                               36


<210> SEQ ID NO 4
<211> LENGTH: 40
<212> TYPE: DNA
<213> ORGANISM: Artificial Sequence
<220> FEATURE:
<223> OTHER INFORMATION: synthetic_primer

<400> SEQUENCE: 4

ccgctctaga actagtggat cttaatggaa actgtgttct                           40


<210> SEQ ID NO 5
<211> LENGTH: 38
<212> TYPE: DNA
<213> ORGANISM: Artificial Sequence
<220> FEATURE:
<223> OTHER INFORMATION: synthetic_primer

<400> SEQUENCE: 5
```

```
tagatcgaaa ggtgcacaaa gatgaaacca accaccat                             38


<210> SEQ ID NO 6
<211> LENGTH: 41
<212> TYPE: DNA
<213> ORGANISM: Artificial Sequence
<220> FEATURE:
<223> OTHER INFORMATION: synthetic_primer

<400> SEQUENCE: 6

ccgctctaga actagtggat cttaatggaa actgtgttct t                         41


<210> SEQ ID NO 7
<211> LENGTH: 42
<212> TYPE: DNA
<213> ORGANISM: Artificial Sequence
<220> FEATURE:
<223> OTHER INFORMATION: synthetic_primer

<400> SEQUENCE: 7

tagatcgaaa ggtgcacaaa gatgtcatta aagcaaataa ct                        42


<210> SEQ ID NO 8
<211> LENGTH: 41
<212> TYPE: DNA
<213> ORGANISM: Artificial Sequence
<220> FEATURE:
<223> OTHER INFORMATION: synthetic_primer

<400> SEQUENCE: 8

ccgctctaga actagtggat cttattggaa actgtgttct t                         41


<210> SEQ ID NO 9
<211> LENGTH: 36
<212> TYPE: DNA
<213> ORGANISM: Artificial Sequence
<220> FEATURE:
<223> OTHER INFORMATION: synthetic_primer

<400> SEQUENCE: 9

tagatcgaaa ggtgcacaaa gatgaaaccc accacc                               36


<210> SEQ ID NO 10
<211> LENGTH: 39
<212> TYPE: DNA
<213> ORGANISM: Artificial Sequence
<220> FEATURE:
<223> OTHER INFORMATION: synthetic_primer

<400> SEQUENCE: 10

ccgctctaga actagtggat cttagttaaa tgagtgctc                            39


<210> SEQ ID NO 11
<211> LENGTH: 37
<212> TYPE: DNA
<213> ORGANISM: Artificial Sequence
<220> FEATURE:
<223> OTHER INFORMATION: synthetic_primer

<400> SEQUENCE: 11

tagatcgaaa ggtgcacaaa gatgaaaccg accacca                              37


<210> SEQ ID NO 12
<211> LENGTH: 40
<212> TYPE: DNA
```

-continued

<213> ORGANISM: Artificial Sequence
<220> FEATURE:
<223> OTHER INFORMATION: synthetic_primer

<400> SEQUENCE: 12
ccgctctaga actagtggat cttaatggaa actgtgttct 40

<210> SEQ ID NO 13
<211> LENGTH: 36
<212> TYPE: DNA
<213> ORGANISM: Artificial Sequence
<220> FEATURE:
<223> OTHER INFORMATION: synthetic_primer

<400> SEQUENCE: 13
tagatcgaaa ggtgcacaaa gatgaaaccc accacg 36

<210> SEQ ID NO 14
<211> LENGTH: 38
<212> TYPE: DNA
<213> ORGANISM: Artificial Sequence
<220> FEATURE:
<223> OTHER INFORMATION: synthetic_primer

<400> SEQUENCE: 14
ccgctctaga actagtggat cttactggaa actgtgct 38

<210> SEQ ID NO 15
<211> LENGTH: 44
<212> TYPE: DNA
<213> ORGANISM: Artificial Sequence
<220> FEATURE:
<223> OTHER INFORMATION: synthetic_primer

<400> SEQUENCE: 15
tagatcgaaa ggtgcacaaa gatgaaaact ttaaatcatt taaa 44

<210> SEQ ID NO 16
<211> LENGTH: 39
<212> TYPE: DNA
<213> ORGANISM: Artificial Sequence
<220> FEATURE:
<223> OTHER INFORMATION: synthetic_primer

<400> SEQUENCE: 16
ccgctctaga actagtggat cttagtcatg ttgctctac 39

<210> SEQ ID NO 17
<211> LENGTH: 37
<212> TYPE: DNA
<213> ORGANISM: Artificial Sequence
<220> FEATURE:
<223> OTHER INFORMATION: synthetic_primer

<400> SEQUENCE: 17
tagatcgaaa ggtgcacaaa gatgccagat gtaaccg 37

<210> SEQ ID NO 18
<211> LENGTH: 36
<212> TYPE: DNA
<213> ORGANISM: Artificial Sequence
<220> FEATURE:
<223> OTHER INFORMATION: synthetic_primer

<400> SEQUENCE: 18
ccgctctaga actagtggat ctcatgcgga gaaccc 36

-continued

<210> SEQ ID NO 19
<211> LENGTH: 36
<212> TYPE: DNA
<213> ORGANISM: Artificial Sequence
<220> FEATURE:
<223> OTHER INFORMATION: synthetic_primer

<400> SEQUENCE: 19
tagatcgaaa ggtgcacaaa gatgcctgat gtgacc 36

<210> SEQ ID NO 20
<211> LENGTH: 36
<212> TYPE: DNA
<213> ORGANISM: Artificial Sequence
<220> FEATURE:
<223> OTHER INFORMATION: synthetic_primer

<400> SEQUENCE: 20
ccgctctaga actagtggat ctcatgcgga gaatcc 36

<210> SEQ ID NO 21
<211> LENGTH: 39
<212> TYPE: DNA
<213> ORGANISM: Artificial Sequence
<220> FEATURE:
<223> OTHER INFORMATION: synthetic_primer

<400> SEQUENCE: 21
tagatcgaaa ggtgcacaaa gatgtcggta cataaagaa 39

<210> SEQ ID NO 22
<211> LENGTH: 42
<212> TYPE: DNA
<213> ORGANISM: Artificial Sequence
<220> FEATURE:
<223> OTHER INFORMATION: synthetic_primer

<400> SEQUENCE: 22
ccgctctaga actagtggat cttaatattg ttctttttcg tt 42

<210> SEQ ID NO 23
<211> LENGTH: 36
<212> TYPE: DNA
<213> ORGANISM: Artificial Sequence
<220> FEATURE:
<223> OTHER INFORMATION: synthetic_primer

<400> SEQUENCE: 23
tagatcgaaa ggtgcacaaa gatgaaaccc accacc 36

<210> SEQ ID NO 24
<211> LENGTH: 40
<212> TYPE: DNA
<213> ORGANISM: Artificial Sequence
<220> FEATURE:
<223> OTHER INFORMATION: synthetic_primer

<400> SEQUENCE: 24
ccgctctaga actagtggat cttagttgaa agagtgctct 40

<210> SEQ ID NO 25
<211> LENGTH: 40
<212> TYPE: DNA
<213> ORGANISM: Artificial Sequence
<220> FEATURE:

<223> OTHER INFORMATION: synthetic_primer

<400> SEQUENCE: 25
tagatcgaaa ggtgcacaaa gatgtctaca gcaaaaaaag 40

<210> SEQ ID NO 26
<211> LENGTH: 40
<212> TYPE: DNA
<213> ORGANISM: Artificial Sequence
<220> FEATURE:
<223> OTHER INFORMATION: synthetic_primer

<400> SEQUENCE: 26
ccgctctaga actagtggat cttaatactg ttcatcgtca 40

<210> SEQ ID NO 27
<211> LENGTH: 41
<212> TYPE: DNA
<213> ORGANISM: Artificial Sequence
<220> FEATURE:
<223> OTHER INFORMATION: synthetic_primer

<400> SEQUENCE: 27
cttgatatcg aattcctgca ttcagggtag ttgactaaag a 41

<210> SEQ ID NO 28
<211> LENGTH: 17
<212> TYPE: DNA
<213> ORGANISM: Artificial Sequence
<220> FEATURE:
<223> OTHER INFORMATION: synthetic_primer

<400> SEQUENCE: 28
ctttgtgcac ctttcga 17

<210> SEQ ID NO 29
<211> LENGTH: 40
<212> TYPE: DNA
<213> ORGANISM: Artificial Sequence
<220> FEATURE:
<223> OTHER INFORMATION: synthetic_primer

<400> SEQUENCE: 29
tgaattcgag ctcggtaccc gaaatagcgc ttgatgaatc 40

<210> SEQ ID NO 30
<211> LENGTH: 40
<212> TYPE: DNA
<213> ORGANISM: Artificial Sequence
<220> FEATURE:
<223> OTHER INFORMATION: synthetic_primer

<400> SEQUENCE: 30
ggttgctacc tgcacccggg gggcatgagt atagatgtga 40

<210> SEQ ID NO 31
<211> LENGTH: 40
<212> TYPE: DNA
<213> ORGANISM: Artificial Sequence
<220> FEATURE:
<223> OTHER INFORMATION: synthetic_primer

<400> SEQUENCE: 31
ctatactcat gccccccggg tgcaggtagc aaccacaaag 40

-continued

<210> SEQ ID NO 32
<211> LENGTH: 40
<212> TYPE: DNA
<213> ORGANISM: Artificial Sequence
<220> FEATURE:
<223> OTHER INFORMATION: synthetic_primer

<400> SEQUENCE: 32
gtcgactcta gaggatcccc tatgtggcgt tgggtgcagc 40

<210> SEQ ID NO 33
<211> LENGTH: 40
<212> TYPE: DNA
<213> ORGANISM: Artificial Sequence
<220> FEATURE:
<223> OTHER INFORMATION: synthetic_primer

<400> SEQUENCE: 33
catctatact catgcccccc ttcagggtag ttgactaaag 40

<210> SEQ ID NO 34
<211> LENGTH: 40
<212> TYPE: DNA
<213> ORGANISM: Artificial Sequence
<220> FEATURE:
<223> OTHER INFORMATION: synthetic_primer

<400> SEQUENCE: 34
tgtggttgct acctgcaccc ttaatggaaa ctgtgttctt 40

<210> SEQ ID NO 35
<211> LENGTH: 20
<212> TYPE: DNA
<213> ORGANISM: Artificial Sequence
<220> FEATURE:
<223> OTHER INFORMATION: synthetic_primer

<400> SEQUENCE: 35
cccacccggt gtcattcgac 20

<210> SEQ ID NO 36
<211> LENGTH: 19
<212> TYPE: DNA
<213> ORGANISM: Artificial Sequence
<220> FEATURE:
<223> OTHER INFORMATION: synthetic_primer

<400> SEQUENCE: 36
gcgcatccag ctcatcggt 19

<210> SEQ ID NO 37
<211> LENGTH: 264
<212> TYPE: PRT
<213> ORGANISM: Artificial Sequence
<220> FEATURE:
<223> OTHER INFORMATION: synthetic_PanB WT

<400> SEQUENCE: 37

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp

-continued

```
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 38
<211> LENGTH: 40
<212> TYPE: DNA
<213> ORGANISM: Artificial Sequence
<220> FEATURE:
<223> OTHER INFORMATION: synthetic_primer

<400> SEQUENCE: 38
gtttctacca gccactcgga gccttcaatt ttgaccatgt 40

<210> SEQ ID NO 39
<211> LENGTH: 40
<212> TYPE: DNA
<213> ORGANISM: Artificial Sequence
<220> FEATURE:
<223> OTHER INFORMATION: synthetic_primer

<400> SEQUENCE: 39
acatggtcaa aattgaaggc tccgagtggc tggtagaaac 40

<210> SEQ ID NO 40
<211> LENGTH: 40
<212> TYPE: DNA
<213> ORGANISM: Artificial Sequence
<220> FEATURE:
<223> OTHER INFORMATION: synthetic_primer

<400> SEQUENCE: 40
gtttctacca gccactcgca gccttcaatt ttgaccatgt 40

<210> SEQ ID NO 41

-continued

<211> LENGTH: 40
<212> TYPE: DNA
<213> ORGANISM: Artificial Sequence
<220> FEATURE:
<223> OTHER INFORMATION: synthetic_primer

<400> SEQUENCE: 41
acatggtcaa aattgaaggc tgcgagtggc tggtagaaac 40

<210> SEQ ID NO 42
<211> LENGTH: 40
<212> TYPE: DNA
<213> ORGANISM: Artificial Sequence
<220> FEATURE:
<223> OTHER INFORMATION: synthetic_primer

<400> SEQUENCE: 42
gtttctacca gccactccag gccttcaatt ttgaccatgt 40

<210> SEQ ID NO 43
<211> LENGTH: 40
<212> TYPE: DNA
<213> ORGANISM: Artificial Sequence
<220> FEATURE:
<223> OTHER INFORMATION: synthetic_primer

<400> SEQUENCE: 43
acatggtcaa aattgaaggc ctggagtggc tggtagaaac 40

<210> SEQ ID NO 44
<211> LENGTH: 40
<212> TYPE: DNA
<213> ORGANISM: Artificial Sequence
<220> FEATURE:
<223> OTHER INFORMATION: synthetic_primer

<400> SEQUENCE: 44
gtttctacca gccactcgat gccttcaatt ttgaccatgt 40

<210> SEQ ID NO 45
<211> LENGTH: 40
<212> TYPE: DNA
<213> ORGANISM: Artificial Sequence
<220> FEATURE:
<223> OTHER INFORMATION: synthetic_primer

<400> SEQUENCE: 45
acatggtcaa aattgaaggc atcgagtggc tggtagaaac 40

<210> SEQ ID NO 46
<211> LENGTH: 40
<212> TYPE: DNA
<213> ORGANISM: Artificial Sequence
<220> FEATURE:
<223> OTHER INFORMATION: synthetic_primer

<400> SEQUENCE: 46
gtttctacca gccactcggt gccttcaatt ttgaccatgt 40

<210> SEQ ID NO 47
<211> LENGTH: 40
<212> TYPE: DNA
<213> ORGANISM: Artificial Sequence
<220> FEATURE:
<223> OTHER INFORMATION: synthetic_primer

<400> SEQUENCE: 47

-continued acatggtcaa aattgaaggc accgagtggc tggtagaaac 40

<210> SEQ ID NO 48
<211> LENGTH: 40
<212> TYPE: DNA
<213> ORGANISM: Artificial Sequence
<220> FEATURE:
<223> OTHER INFORMATION: synthetic_primer

<400> SEQUENCE: 48
gtttctacca gccactccac gccttcaatt ttgaccatgt 40

<210> SEQ ID NO 49
<211> LENGTH: 40
<212> TYPE: DNA
<213> ORGANISM: Artificial Sequence
<220> FEATURE:
<223> OTHER INFORMATION: synthetic_primer

<400> SEQUENCE: 49
acatggtcaa aattgaaggc gtggagtggc tggtagaaac 40

<210> SEQ ID NO 50
<211> LENGTH: 40
<212> TYPE: DNA
<213> ORGANISM: Artificial Sequence
<220> FEATURE:
<223> OTHER INFORMATION: synthetic_primer

<400> SEQUENCE: 50
gtttctacca gccactccat gccttcaatt ttgaccatgt 40

<210> SEQ ID NO 51
<211> LENGTH: 40
<212> TYPE: DNA
<213> ORGANISM: Artificial Sequence
<220> FEATURE:
<223> OTHER INFORMATION: synthetic_primer

<400> SEQUENCE: 51
acatggtcaa aattgaaggc atggagtggc tggtagaaac 40

<210> SEQ ID NO 52
<211> LENGTH: 40
<212> TYPE: DNA
<213> ORGANISM: Artificial Sequence
<220> FEATURE:
<223> OTHER INFORMATION: synthetic_primer

<400> SEQUENCE: 52
gtttctacca gccactcatc gccttcaatt ttgaccatgt 40

<210> SEQ ID NO 53
<211> LENGTH: 40
<212> TYPE: DNA
<213> ORGANISM: Artificial Sequence
<220> FEATURE:
<223> OTHER INFORMATION: synthetic_primer

<400> SEQUENCE: 53
acatggtcaa aattgaaggc gatgagtggc tggtagaaac 40

<210> SEQ ID NO 54
<211> LENGTH: 40
<212> TYPE: DNA

<213> ORGANISM: Artificial Sequence
<220> FEATURE:
<223> OTHER INFORMATION: synthetic_primer

<400> SEQUENCE: 54
gtttctacca gccactcttc gccttcaatt ttgaccatgt 40

<210> SEQ ID NO 55
<211> LENGTH: 40
<212> TYPE: DNA
<213> ORGANISM: Artificial Sequence
<220> FEATURE:
<223> OTHER INFORMATION: synthetic_primer

<400> SEQUENCE: 55
acatggtcaa aattgaaggc gaagagtggc tggtagaaac 40

<210> SEQ ID NO 56
<211> LENGTH: 40
<212> TYPE: DNA
<213> ORGANISM: Artificial Sequence
<220> FEATURE:
<223> OTHER INFORMATION: synthetic_primer

<400> SEQUENCE: 56
gtttctacca gccactcgtt gccttcaatt ttgaccatgt 40

<210> SEQ ID NO 57
<211> LENGTH: 40
<212> TYPE: DNA
<213> ORGANISM: Artificial Sequence
<220> FEATURE:
<223> OTHER INFORMATION: synthetic_primer

<400> SEQUENCE: 57
acatggtcaa aattgaaggc aacgagtggc tggtagaaac 40

<210> SEQ ID NO 58
<211> LENGTH: 40
<212> TYPE: DNA
<213> ORGANISM: Artificial Sequence
<220> FEATURE:
<223> OTHER INFORMATION: synthetic_primer

<400> SEQUENCE: 58
gtttctacca gccactcctg gccttcaatt ttgaccatgt 40

<210> SEQ ID NO 59
<211> LENGTH: 40
<212> TYPE: DNA
<213> ORGANISM: Artificial Sequence
<220> FEATURE:
<223> OTHER INFORMATION: synthetic_primer

<400> SEQUENCE: 59
acatggtcaa aattgaaggc caggagtggc tggtagaaac 40

<210> SEQ ID NO 60
<211> LENGTH: 40
<212> TYPE: DNA
<213> ORGANISM: Artificial Sequence
<220> FEATURE:
<223> OTHER INFORMATION: synthetic_primer

<400> SEQUENCE: 60
gtttctacca gccactctgc gccttcaatt ttgaccatgt 40

<210> SEQ ID NO 61
<211> LENGTH: 40
<212> TYPE: DNA
<213> ORGANISM: Artificial Sequence
<220> FEATURE:
<223> OTHER INFORMATION: synthetic_primer

<400> SEQUENCE: 61
acatggtcaa aattgaaggc gcagagtggc tggtagaaac 40

<210> SEQ ID NO 62
<211> LENGTH: 264
<212> TYPE: PRT
<213> ORGANISM: Artificial Sequence
<220> FEATURE:
<223> OTHER INFORMATION: synthetic_PanB with G116A mutation

<400> SEQUENCE: 62

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Ala Glu Trp Leu Val Glu Thr Val Gln Met Leu Thr Glu
115 120 125

Arg Ala Val Pro Val Cys Gly His Leu Gly Leu Thr Pro Gln Ser Val
130 135 140

Asn Ile Phe Gly Gly Tyr Lys Val Gln Gly Arg Gly Asp Glu Ala Gly
145 150 155 160

Asp Gln Leu Leu Ser Asp Ala Leu Ala Leu Glu Ala Ala Gly Ala Gln
165 170 175

Leu Leu Val Leu Glu Cys Val Pro Val Glu Leu Ala Lys Arg Ile Thr
180 185 190

Glu Ala Leu Ala Ile Pro Val Ile Gly Ile Gly Ala Gly Asn Val Thr
195 200 205

Asp Gly Gln Ile Leu Val Met His Asp Ala Phe Gly Ile Thr Gly Gly
210 215 220

His Ile Pro Lys Phe Ala Lys Asn Phe Leu Ala Glu Thr Gly Asp Ile
225 230 235 240

Arg Ala Ala Val Arg Gln Tyr Met Ala Glu Val Glu Ser Gly Val Tyr
245 250 255

Pro Gly Glu Glu His Ser Phe His
260

<210> SEQ ID NO 63
<211> LENGTH: 264
<212> TYPE: PRT
<213> ORGANISM: Artificial Sequence -continued
<220> FEATURE:
<223> OTHER INFORMATION: synthetic_PanB with G116N mutation

<400> SEQUENCE: 63

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Asn Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260

<210> SEQ ID NO 64
<211> LENGTH: 264
<212> TYPE: PRT
<213> ORGANISM: Artificial Sequence
<220> FEATURE:
<223> OTHER INFORMATION: synthetic_PanB with G116T mutation

<400> SEQUENCE: 64

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu

-continued

```
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Thr Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 65
<211> LENGTH: 264
<212> TYPE: PRT
<213> ORGANISM: Artificial Sequence
<220> FEATURE:
<223> OTHER INFORMATION: synthetic_PanB with G116E mutation

<400> SEQUENCE: 65

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Glu Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
```

-continued

```
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 66
<211> LENGTH: 264
<212> TYPE: PRT
<213> ORGANISM: Artificial Sequence
<220> FEATURE:
<223> OTHER INFORMATION: synthetic_PanB with G116S mutation

<400> SEQUENCE: 66

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Ser Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
```

260

<210> SEQ ID NO 67
<211> LENGTH: 264
<212> TYPE: PRT
<213> ORGANISM: Artificial Sequence
<220> FEATURE:
<223> OTHER INFORMATION: synthetic_PanB with G116V mutation

<400> SEQUENCE: 67

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Val Glu Trp Leu Val Glu Thr Val Gln Met Leu Thr Glu
115 120 125

Arg Ala Val Pro Val Cys Gly His Leu Gly Leu Thr Pro Gln Ser Val
130 135 140

Asn Ile Phe Gly Gly Tyr Lys Val Gln Gly Arg Gly Asp Glu Ala Gly
145 150 155 160

Asp Gln Leu Leu Ser Asp Ala Leu Ala Leu Glu Ala Ala Gly Ala Gln
165 170 175

Leu Leu Val Leu Glu Cys Val Pro Val Glu Leu Ala Lys Arg Ile Thr
180 185 190

Glu Ala Leu Ala Ile Pro Val Ile Gly Ile Gly Ala Gly Asn Val Thr
195 200 205

Asp Gly Gln Ile Leu Val Met His Asp Ala Phe Gly Ile Thr Gly Gly
210 215 220

His Ile Pro Lys Phe Ala Lys Asn Phe Leu Ala Glu Thr Gly Asp Ile
225 230 235 240

Arg Ala Ala Val Arg Gln Tyr Met Ala Glu Val Glu Ser Gly Val Tyr
245 250 255

Pro Gly Glu Glu His Ser Phe His
260

<210> SEQ ID NO 68
<211> LENGTH: 264
<212> TYPE: PRT
<213> ORGANISM: Artificial Sequence
<220> FEATURE:
<223> OTHER INFORMATION: synthetic_PanB with G116I mutation

<400> SEQUENCE: 68

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Ile Glu Trp Leu Val Glu Thr Val Gln Met Leu Thr Glu
115 120 125

Arg Ala Val Pro Val Cys Gly His Leu Gly Leu Thr Pro Gln Ser Val
130 135 140

Asn Ile Phe Gly Gly Tyr Lys Val Gln Gly Arg Gly Asp Glu Ala Gly
145 150 155 160

Asp Gln Leu Leu Ser Asp Ala Leu Ala Leu Glu Ala Ala Gly Ala Gln
165 170 175

Leu Leu Val Leu Glu Cys Val Pro Val Glu Leu Ala Lys Arg Ile Thr
180 185 190

Glu Ala Leu Ala Ile Pro Val Ile Gly Ile Gly Ala Gly Asn Val Thr
195 200 205

Asp Gly Gln Ile Leu Val Met His Asp Ala Phe Gly Ile Thr Gly Gly
210 215 220

His Ile Pro Lys Phe Ala Lys Asn Phe Leu Ala Glu Thr Gly Asp Ile
225 230 235 240

Arg Ala Ala Val Arg Gln Tyr Met Ala Glu Val Glu Ser Gly Val Tyr
245 250 255

Pro Gly Glu Glu His Ser Phe His
260

<210> SEQ ID NO 69
<211> LENGTH: 264
<212> TYPE: PRT
<213> ORGANISM: Artificial Sequence
<220> FEATURE:
<223> OTHER INFORMATION: synthetic_PanB with G116L mutation

<400> SEQUENCE: 69

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Leu Glu Trp Leu Val Glu Thr Val Gln Met Leu Thr Glu
115 120 125

```
Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 70
<211> LENGTH: 264
<212> TYPE: PRT
<213> ORGANISM: Artificial Sequence
<220> FEATURE:
<223> OTHER INFORMATION: synthetic_PanB with G116D mutation

<400> SEQUENCE: 70

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Asp Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220
```

```
His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 71
<211> LENGTH: 264
<212> TYPE: PRT
<213> ORGANISM: Artificial Sequence
<220> FEATURE:
<223> OTHER INFORMATION: synthetic_PanB with G116C mutation

<400> SEQUENCE: 71

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Cys Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 72
<211> LENGTH: 264
<212> TYPE: PRT
<213> ORGANISM: Artificial Sequence
<220> FEATURE:
<223> OTHER INFORMATION: synthetic_PanB with G116Q mutation

<400> SEQUENCE: 72
```

-continued

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gln Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260

<210> SEQ ID NO 73
<211> LENGTH: 264
<212> TYPE: PRT
<213> ORGANISM: Artificial Sequence
<220> FEATURE:
<223> OTHER INFORMATION: synthetic_PanB with G116M mutation

<400> SEQUENCE: 73

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

-continued

```
Phe Glu Asn Ala Ala Thr Val Met Arg Ala Gly Ala Asn Met Val Lys
            100                 105                 110

Ile Glu Gly Met Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 74
<211> LENGTH: 40
<212> TYPE: DNA
<213> ORGANISM: Artificial Sequence
<220> FEATURE:
<223> OTHER INFORMATION: primer

<400> SEQUENCE: 74
agatcgaaag gtgcacaaag atgaaaccga ccaccatctc 40

<210> SEQ ID NO 75
<211> LENGTH: 40
<212> TYPE: DNA
<213> ORGANISM: Artificial Sequence
<220> FEATURE:
<223> OTHER INFORMATION: primer

<400> SEQUENCE: 75
aggggcgcgg cgatgaacgc ggcgatcaac tgctcagcga 40

<210> SEQ ID NO 76
<211> LENGTH: 40
<212> TYPE: DNA
<213> ORGANISM: Artificial Sequence
<220> FEATURE:
<223> OTHER INFORMATION: primer

<400> SEQUENCE: 76
ctgagcagtt gatcgccgcg ttcatcgccg cgcccctgaa 40

<210> SEQ ID NO 77
<211> LENGTH: 40
<212> TYPE: DNA
<213> ORGANISM: Artificial Sequence
<220> FEATURE:
<223> OTHER INFORMATION: primer

<400> SEQUENCE: 77
cgctctagaa ctagtggatc ttaatggaaa ctgtgttctt 40

<210> SEQ ID NO 78
<211> LENGTH: 40
<212> TYPE: DNA
<213> ORGANISM: Artificial Sequence
<220> FEATURE:
<223> OTHER INFORMATION: primer

<400> SEQUENCE: 78
aggggcgcgg cgatgaatcc ggcgatcaac tgctcagcga 40

<210> SEQ ID NO 79
<211> LENGTH: 40
<212> TYPE: DNA
<213> ORGANISM: Artificial Sequence
<220> FEATURE:
<223> OTHER INFORMATION: primer

<400> SEQUENCE: 79
ctgagcagtt gatcgccgga ttcatcgccg cgcccctgaa 40

<210> SEQ ID NO 80
<211> LENGTH: 40
<212> TYPE: DNA
<213> ORGANISM: Artificial Sequence
<220> FEATURE:
<223> OTHER INFORMATION: primer

<400> SEQUENCE: 80
aggggcgcgg cgatgaatac ggcgatcaac tgctcagcga 40

<210> SEQ ID NO 81
<211> LENGTH: 40
<212> TYPE: DNA
<213> ORGANISM: Artificial Sequence
<220> FEATURE:
<223> OTHER INFORMATION: primer

<400> SEQUENCE: 81
ctgagcagtt gatcgccgta ttcatcgccg cgcccctgaa 40

<210> SEQ ID NO 82
<211> LENGTH: 40
<212> TYPE: DNA
<213> ORGANISM: Artificial Sequence
<220> FEATURE:
<223> OTHER INFORMATION: primer

<400> SEQUENCE: 82
aggggcgcgg cgatgaatgc ggcgatcaac tgctcagcga 40

<210> SEQ ID NO 83
<211> LENGTH: 40
<212> TYPE: DNA
<213> ORGANISM: Artificial Sequence
<220> FEATURE:
<223> OTHER INFORMATION: primer

<400> SEQUENCE: 83
ctgagcagtt gatcgccgca ttcatcgccg cgcccctgaa 40

<210> SEQ ID NO 84
<211> LENGTH: 40
<212> TYPE: DNA

<213> ORGANISM: Artificial Sequence
<220> FEATURE:
<223> OTHER INFORMATION: primer

<400> SEQUENCE: 84
aggggcgcgg cgatgaacca ggcgatcaac tgctcagcga 40

<210> SEQ ID NO 85
<211> LENGTH: 40
<212> TYPE: DNA
<213> ORGANISM: Artificial Sequence
<220> FEATURE:
<223> OTHER INFORMATION: primer

<400> SEQUENCE: 85
ctgagcagtt gatcgcctgg ttcatcgccg cgcccctgaa 40

<210> SEQ ID NO 86
<211> LENGTH: 40
<212> TYPE: DNA
<213> ORGANISM: Artificial Sequence
<220> FEATURE:
<223> OTHER INFORMATION: primer

<400> SEQUENCE: 86
aggggcgcgg cgatgaacac ggcgatcaac tgctcagcga 40

<210> SEQ ID NO 87
<211> LENGTH: 40
<212> TYPE: DNA
<213> ORGANISM: Artificial Sequence
<220> FEATURE:
<223> OTHER INFORMATION: primer

<400> SEQUENCE: 87
ctgagcagtt gatcgccgtg ttcatcgccg cgcccctgaa 40

<210> SEQ ID NO 88
<211> LENGTH: 40
<212> TYPE: DNA
<213> ORGANISM: Artificial Sequence
<220> FEATURE:
<223> OTHER INFORMATION: primer

<400> SEQUENCE: 88
aggggcgcgg cgatgaactg ggcgatcaac tgctcagcga 40

<210> SEQ ID NO 89
<211> LENGTH: 40
<212> TYPE: DNA
<213> ORGANISM: Artificial Sequence
<220> FEATURE:
<223> OTHER INFORMATION: primer

<400> SEQUENCE: 89
ctgagcagtt gatcgcccag ttcatcgccg cgcccctgaa 40

<210> SEQ ID NO 90
<211> LENGTH: 40
<212> TYPE: DNA
<213> ORGANISM: Artificial Sequence
<220> FEATURE:
<223> OTHER INFORMATION: primer

<400> SEQUENCE: 90
aggggcgcgg cgatgaaatc ggcgatcaac tgctcagcga 40

<210> SEQ ID NO 91
<211> LENGTH: 40
<212> TYPE: DNA
<213> ORGANISM: Artificial Sequence
<220> FEATURE:
<223> OTHER INFORMATION: primer

<400> SEQUENCE: 91
ctgagcagtt gatcgccgat ttcatcgccg cgcccctgaa 40

<210> SEQ ID NO 92
<211> LENGTH: 40
<212> TYPE: DNA
<213> ORGANISM: Artificial Sequence
<220> FEATURE:
<223> OTHER INFORMATION: primer

<400> SEQUENCE: 92
aggggcgcgg cgatgaaacc ggcgatcaac tgctcagcga 40

<210> SEQ ID NO 93
<211> LENGTH: 40
<212> TYPE: DNA
<213> ORGANISM: Artificial Sequence
<220> FEATURE:
<223> OTHER INFORMATION: primer

<400> SEQUENCE: 93
ctgagcagtt gatcgccggt ttcatcgccg cgcccctgaa 40

<210> SEQ ID NO 94
<211> LENGTH: 40
<212> TYPE: DNA
<213> ORGANISM: Artificial Sequence
<220> FEATURE:
<223> OTHER INFORMATION: primer

<400> SEQUENCE: 94
aggggcgcgg cgatgaaaag ggcgatcaac tgctcagcga 40

<210> SEQ ID NO 95
<211> LENGTH: 40
<212> TYPE: DNA
<213> ORGANISM: Artificial Sequence
<220> FEATURE:
<223> OTHER INFORMATION: primer

<400> SEQUENCE: 95
ctgagcagtt gatcgccctt ttcatcgccg cgcccctgaa 40

<210> SEQ ID NO 96
<211> LENGTH: 40
<212> TYPE: DNA
<213> ORGANISM: Artificial Sequence
<220> FEATURE:
<223> OTHER INFORMATION: primer

<400> SEQUENCE: 96
aggggcgcgg cgatgaagtg ggcgatcaac tgctcagcga 40

<210> SEQ ID NO 97
<211> LENGTH: 40
<212> TYPE: DNA
<213> ORGANISM: Artificial Sequence
<220> FEATURE:

<223> OTHER INFORMATION: primer

<400> SEQUENCE: 97
ctgagcagtt gatcgcccac ttcatcgccg cgcccctgaa 40

<210> SEQ ID NO 98
<211> LENGTH: 40
<212> TYPE: DNA
<213> ORGANISM: Artificial Sequence
<220> FEATURE:
<223> OTHER INFORMATION: primer

<400> SEQUENCE: 98
aggggcgcgg cgatgaaatg ggcgatcaac tgctcagcga 40

<210> SEQ ID NO 99
<211> LENGTH: 40
<212> TYPE: DNA
<213> ORGANISM: Artificial Sequence
<220> FEATURE:
<223> OTHER INFORMATION: primer

<400> SEQUENCE: 99
ctgagcagtt gatcgcccat ttcatcgccg cgcccctgaa 40

<210> SEQ ID NO 100
<211> LENGTH: 40
<212> TYPE: DNA
<213> ORGANISM: Artificial Sequence
<220> FEATURE:
<223> OTHER INFORMATION: primer

<400> SEQUENCE: 100
aggggcgcgg cgatgaagat ggcgatcaac tgctcagcga 40

<210> SEQ ID NO 101
<211> LENGTH: 40
<212> TYPE: DNA
<213> ORGANISM: Artificial Sequence
<220> FEATURE:
<223> OTHER INFORMATION: primer

<400> SEQUENCE: 101
ctgagcagtt gatcgccatc ttcatcgccg cgcccctgaa 40

<210> SEQ ID NO 102
<211> LENGTH: 40
<212> TYPE: DNA
<213> ORGANISM: Artificial Sequence
<220> FEATURE:
<223> OTHER INFORMATION: primer

<400> SEQUENCE: 102
aggggcgcgg cgatgaacag ggcgatcaac tgctcagcga 40

<210> SEQ ID NO 103
<211> LENGTH: 40
<212> TYPE: DNA
<213> ORGANISM: Artificial Sequence
<220> FEATURE:
<223> OTHER INFORMATION: primer

<400> SEQUENCE: 103
ctgagcagtt gatcgccctg ttcatcgccg cgcccctgaa 40

<210> SEQ ID NO 104
<211> LENGTH: 40
<212> TYPE: DNA
<213> ORGANISM: Artificial Sequence
<220> FEATURE:
<223> OTHER INFORMATION: primer

<400> SEQUENCE: 104
aggggcgcgg cgatgaaaac ggcgatcaac tgctcagcga 40

<210> SEQ ID NO 105
<211> LENGTH: 40
<212> TYPE: DNA
<213> ORGANISM: Artificial Sequence
<220> FEATURE:
<223> OTHER INFORMATION: primer

<400> SEQUENCE: 105
ctgagcagtt gatcgccgtt ttcatcgccg cgcccctgaa 40

<210> SEQ ID NO 106
<211> LENGTH: 40
<212> TYPE: DNA
<213> ORGANISM: Artificial Sequence
<220> FEATURE:
<223> OTHER INFORMATION: primer

<400> SEQUENCE: 106
aggggcgcgg cgatgaacag ggcgatcaac tgctcagcga 40

<210> SEQ ID NO 107
<211> LENGTH: 40
<212> TYPE: DNA
<213> ORGANISM: Artificial Sequence
<220> FEATURE:
<223> OTHER INFORMATION: primer

<400> SEQUENCE: 107
ctgagcagtt gatcgccctg ttcatcgccg cgcccctgaa 40

<210> SEQ ID NO 108
<211> LENGTH: 40
<212> TYPE: DNA
<213> ORGANISM: Artificial Sequence
<220> FEATURE:
<223> OTHER INFORMATION: primer

<400> SEQUENCE: 108
cttgatatcg aattcctgca ttcagggtag ttgactaaag 40

<210> SEQ ID NO 109
<211> LENGTH: 40
<212> TYPE: DNA
<213> ORGANISM: Artificial Sequence
<220> FEATURE:
<223> OTHER INFORMATION: primer

<400> SEQUENCE: 109
gagatggtgg tcggtttcat ctttgtgcac ctttcgatct 40

<210> SEQ ID NO 110
<211> LENGTH: 264
<212> TYPE: PRT
<213> ORGANISM: Artificial Sequence
<220> FEATURE:
<223> OTHER INFORMATION: PanB with A159L mutation -continued

<400> SEQUENCE: 110

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Leu Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 111
<211> LENGTH: 264
<212> TYPE: PRT
<213> ORGANISM: Artificial Sequence
<220> FEATURE:
<223> OTHER INFORMATION: PanB with A159R mutation

<400> SEQUENCE: 111

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
```

-continued

```
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Arg Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 112
<211> LENGTH: 264
<212> TYPE: PRT
<213> ORGANISM: Artificial Sequence
<220> FEATURE:
<223> OTHER INFORMATION: PanB with A159S mutation

<400> SEQUENCE: 112

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ser Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
```

```
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 113
<211> LENGTH: 264
<212> TYPE: PRT
<213> ORGANISM: Artificial Sequence
<220> FEATURE:
<223> OTHER INFORMATION: PanB with A159Y mutation

<400> SEQUENCE: 113

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Tyr Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 114
<211> LENGTH: 264
<212> TYPE: PRT
<213> ORGANISM: Artificial Sequence
<220> FEATURE:
<223> OTHER INFORMATION: PanB with A159C mutation

<400> SEQUENCE: 114

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Cys Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 115
<211> LENGTH: 264
<212> TYPE: PRT
<213> ORGANISM: Artificial Sequence
<220> FEATURE:
<223> OTHER INFORMATION: PanB with A159P mutation

<400> SEQUENCE: 115

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45
```

-continued

```
Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Pro Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 116
<211> LENGTH: 264
<212> TYPE: PRT
<213> ORGANISM: Artificial Sequence
<220> FEATURE:
<223> OTHER INFORMATION: PanB with A159H mutation

<400> SEQUENCE: 116

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140
```

```
Asn Ile Phe Gly Gly Tyr Lys Val Gln Gly Arg Gly Asp Glu His Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 117
<211> LENGTH: 264
<212> TYPE: PRT
<213> ORGANISM: Artificial Sequence
<220> FEATURE:
<223> OTHER INFORMATION: PanB with A159I mutation

<400> SEQUENCE: 117

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ile Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240
```

-continued

```
Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 118
<211> LENGTH: 264
<212> TYPE: PRT
<213> ORGANISM: Artificial Sequence
<220> FEATURE:
<223> OTHER INFORMATION: PanB with A159T mutation

<400> SEQUENCE: 118

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Thr Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 119
<211> LENGTH: 264
<212> TYPE: PRT
<213> ORGANISM: Artificial Sequence
<220> FEATURE:
<223> OTHER INFORMATION: PanB with A159K mutation

<400> SEQUENCE: 119

```
Met Lys Pro Thr Thr Ile Ser Leu Leu Gln Lys Tyr Lys Gln Glu Lys
1               5                   10                  15
```

```
Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Lys Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 120
<211> LENGTH: 264
<212> TYPE: PRT
<213> ORGANISM: Artificial Sequence
<220> FEATURE:
<223> OTHER INFORMATION: PanB with A159V mutation

<400> SEQUENCE: 120

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110
```

```
Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Val Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 121
<211> LENGTH: 264
<212> TYPE: PRT
<213> ORGANISM: Artificial Sequence
<220> FEATURE:
<223> OTHER INFORMATION: PanB with A159M mutation

<400> SEQUENCE: 121

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Met Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205
```

```
Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 122
<211> LENGTH: 264
<212> TYPE: PRT
<213> ORGANISM: Artificial Sequence
<220> FEATURE:
<223> OTHER INFORMATION: PanB with A159D mutation

<400> SEQUENCE: 122

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Asp Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 123
<211> LENGTH: 264
<212> TYPE: PRT
<213> ORGANISM: Artificial Sequence
```

<220> FEATURE:
<223> OTHER INFORMATION: PanB with A159E mutation

<400> SEQUENCE: 123

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Glu Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 124
<211> LENGTH: 264
<212> TYPE: PRT
<213> ORGANISM: Artificial Sequence
<220> FEATURE:
<223> OTHER INFORMATION: PanB with A159N mutation

<400> SEQUENCE: 124

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
```

```
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Asn Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 125
<211> LENGTH: 264
<212> TYPE: PRT
<213> ORGANISM: Artificial Sequence
<220> FEATURE:
<223> OTHER INFORMATION: PanB with A159Q mutation

<400> SEQUENCE: 125

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Gln Gly
145                 150                 155                 160

Asp Gln Leu Leu Ser Asp Ala Leu Ala Leu Glu Ala Ala Gly Ala Gln
```

```
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 126
<211> LENGTH: 40
<212> TYPE: DNA
<213> ORGANISM: Artificial Sequence
<220> FEATURE:
<223> OTHER INFORMATION: primer

<400> SEQUENCE: 126

gtttctacca gccactcggc gccttcaatt ttgaccatgt                            40


<210> SEQ ID NO 127
<211> LENGTH: 40
<212> TYPE: DNA
<213> ORGANISM: Artificial Sequence
<220> FEATURE:
<223> OTHER INFORMATION: primer

<400> SEQUENCE: 127

tggtcaaaat tgaaggcgcc gagtggctgg tagaaaccgt                            40


<210> SEQ ID NO 128
<211> LENGTH: 264
<212> TYPE: PRT
<213> ORGANISM: Artificial Sequence
<220> FEATURE:
<223> OTHER INFORMATION: PanB with G116A and A159L mutation

<400> SEQUENCE: 128

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Ala Glu Trp Leu Val Glu Thr Val Gln Met Leu Thr Glu
        115                 120                 125

Arg Ala Val Pro Val Cys Gly His Leu Gly Leu Thr Pro Gln Ser Val
```

-continued

```
    130                 135                 140

Asn Ile Phe Gly Gly Tyr Lys Val Gln Gly Arg Gly Asp Glu Leu Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```